United States Patent
Edwards et al.

(10) Patent No.: US 9,475,047 B2
(45) Date of Patent: Oct. 25, 2016

(54) IMMUNOASSAYS, METHODS FOR CARRYING OUT IMMUNOASSAYS, IMMUNOASSAY KITS AND METHOD FOR MANUFACTURING IMMUNOASSAY KITS

(75) Inventors: Alexander Daniel Edwards, Reading (GB); Nuno Miguel Fernandes Reis, Cambridge (GB); Malcolm Robert Mackley, Cambridge (GB); Nigel Kenneth Harry Slater, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 131 days.

(21) Appl. No.: 13/636,913

(22) PCT Filed: Mar. 23, 2011

(86) PCT No.: PCT/GB2011/000414
§ 371 (c)(1),
(2), (4) Date: Sep. 24, 2012

(87) PCT Pub. No.: WO2011/117579
PCT Pub. Date: Sep. 29, 2011

(65) Prior Publication Data
US 2013/0011913 A1    Jan. 10, 2013

(30) Foreign Application Priority Data
Mar. 26, 2010   (GB) .................................. 10055191.0

(51) Int. Cl.
*B01L 3/00* (2006.01)
*G01N 33/543* (2006.01)

(52) U.S. Cl.
CPC ... *B01L 3/502715* (2013.01); *G01N 33/54366* (2013.01); *B01L 2300/0636* (2013.01); *B01L 2300/0654* (2013.01); *B01L 2300/0816* (2013.01); *B01L 2300/0838* (2013.01)

(58) Field of Classification Search
CPC ............... B01L 2300/0816; B01L 2300/0861; B01L 2300/0877; B01L 2300/168; B01L 2300/0887; B01L 3/5027; B01L 3/5025; B01L 2400/0406; B01L 2200/027; G01N 30/466; G01N 30/46; G01N 30/6043; G01N 30/6095; G01N 30/6078; G01N 2035/00158; G01N 2035/00237; G01N 2030/74; G01N 2030/746; G01N 2021/0346; G01N 27/44791; G01N 35/00029
USPC ............ 422/412, 417, 425, 68.1, 69, 82.05, 422/82.09, 502, 503, 504, 507, 527, 554; 435/7.1, 287.1, 287.2, 287.9, 288.3, 435/288.6, 288.7; 436/514, 518, 524–527, 436/805, 824
See application file for complete search history.

(56) References Cited

U.S. PATENT DOCUMENTS 4,116,638 A    9/1978   Kenoff
4,454,235 A    6/1984   Johnson
(Continued)

FOREIGN PATENT DOCUMENTS

EP    0321736 A2    6/1989
EP    1880766 A1    1/2008
(Continued)

OTHER PUBLICATIONS

Bange et al., "Microfluidic immunosensor systems," *Biosensors and Bioelectronics* 20:2488-2503, 2005.
(Continued)

*Primary Examiner* — Erik B Crawford
(74) *Attorney, Agent, or Firm* — Clark & Elbing LLP

(57) ABSTRACT

The invention relates to immunoassays, methods for carrying out immunoassays, immunoassay kits and methods for manufacturing immunoassay kits. In particular, the invention has relevance to capillary (especially microcapillary) immunoassay technology.

22 Claims, 30 Drawing Sheets

(56) References Cited

U.S. PATENT DOCUMENTS

| | | | |
|---|---|---|---|
| 4,590,157 | A | 5/1986 | Chandler et al. |
| 4,716,121 | A | 12/1987 | Block et al. |
| 4,883,760 | A | 11/1989 | Heelies |
| 5,147,607 | A * | 9/1992 | Mochida ............... 422/417 |
| 5,624,850 | A | 4/1997 | Kumar et al. |
| 5,723,345 | A * | 3/1998 | Yamauchi et al. ......... 436/518 |
| 5,976,896 | A | 11/1999 | Kumar et al. |
| 6,059,719 | A * | 5/2000 | Yamamoto et al. ........ 600/127 |
| 6,340,598 | B1 | 1/2002 | Herron et al. |
| 6,517,778 | B1 | 2/2003 | Kumar et al. |
| 6,653,151 | B2 * | 11/2003 | Anderson et al. ......... 436/518 |
| 6,716,629 | B2 | 4/2004 | Hess et al. |
| 8,475,736 | B2 * | 7/2013 | Wimberger-Friedl et al. ............... 422/502 |
| 2002/0094533 | A1 | 7/2002 | Hess et al. |
| 2008/0020453 | A1 * | 1/2008 | Ehben et al. ............ 435/287.2 |
| 2009/0075390 | A1 * | 3/2009 | Linder et al. ............ 436/161 |
| 2010/0144020 | A1 * | 6/2010 | Kim et al. ............... 435/287.1 |
| 2010/0328664 | A1 * | 12/2010 | Luscher .................. 356/338 |

FOREIGN PATENT DOCUMENTS

| | | |
|---|---|---|
| GB | 2408961 A | 6/2005 |
| JP | 2002040028 A | 2/2002 |
| WO | WO-03/042697 A1 | 5/2003 |
| WO | WO-2005/056272 A1 | 6/2005 |
| WO | WO-2006/046054 A1 | 5/2006 |
| WO | WO-2008/044122 A2 | 4/2008 |
| WO | WO-2008/063406 A2 | 5/2008 |
| WO | WO-2009/150549 A2 | 12/2009 |

OTHER PUBLICATIONS

Darton et al., "Fast cation-exchange separation of proteins in a plastic microcapillary disc", *Journal of chromatography*, 1218:1409-1415, 2011.
Edwards et al., "A new technology for fast multiplexed immunoassays", *Journal of Biotechnology* 150S:S204, 2010.
Healey et al., "A rapid semi quantitative capillary enzyme immunoassay for digoxin," *Clinica Chimica Acta*, 134:51-58, 1983.
Hemmilä, "Fluoroimmunoassays and Immunofluorometric Assays," *Clin chem.* 31/3:359-370, 1985.
Henares et al., "Multiple enzyme linked immunosorbent assay system on a capillary-assembled microchip integrating valving and immuno-reaction functions," *Analytica Chimica Acta* 589:173-179, 2007.
Herrmann et al., "Enzymatically-generated fluorescent detection in micro-channels with internal magnetic mixing for the development of parallel microfluidic ELISA," *Lab Chip* 6: 555-560, 2006.
Lionello et al., "Protein adsorption in static microsystems: effect of the surface to volume ratio," *Lab Chip* 5:254-260, 2005.

Mastichiadis et al., "Capillary-based immunoassays, immunosensors and DNA sensors—steps towards integration and multi-analysis," *Trends in Analytical Chemistry*, 27:771-784, 2008.
Mastichiadis et al., "Simultaneous Determination of Pesticides Using a Four-Band Disposable Optical Capillary Immunosensor," *Anal. Chem.* 74:6064-6072, 2002.
Misiakos et al., "A multi-band capillary immunosensor," *Biosensors & Bioelectronics* 13:825-830, 1998.
Nagainis et al., "A rapid quantitative capillary tube enzyme immunoassay for human chorionic gonadotropin in urine," *Clinica Chimica Acta* 160:273-279, 1986.
Petrou et al., "Multi-analyte capillary immunosensor for the determination of hormones in human serum samples," *Biosensors & Bioelectronics* 17:261-268, 2002.
Rindorf et al., "Towards biochips using microstructured optical fiber sensors" *Analytical and bioanalytical chemistry*, 385:1370-1375, 2006.
Rose et al., "GDH biosensor based off-line capillary immunoassay for alkylphenols and their ethoxylates," *Biosensors and Bioelectronics* 17:1033-1043, 2002.
Schroeder et al., "User Configurable Microfluidic Device for Multiplexed Immunoassays Based on DNA-Directed Assembly," *Anal. Chem.* 81: 1275-1279, 2009.
Shekarchi et al., "Capillary Enzyme Immunoassay for Rapid Detection of Herpes Simplex Virus in Clinical Specimens," *Journal of clinical microbiology* 25:320-322, 1987.
Yacoub-George et al., "Automated 10-channel capillary chip immunodetector for biological agents detection," *Biosensors and Bioelectronics* 22:1368-1375, 2007.
Yager et al., "Microfluidic diagnostic technologies for global public health," *Nature*, 442:412-418, 2006.
Zick et al., "Capillary Radioimmunoassay for Insulin," *Eur. J. Nucl. Med.* 5:423-425, 1980.
International Search Report for International Application No. PCT/GB2011/000414, mailed Aug. 2, 2011.
Datasheet for Supreme General Purpose Polystyrene (GPPS) (2 pages).
Product Information for DuPont Teflon FEP 9494 Fluoroplastic Resin, 2013 (2 pages).
Product Information for DuPont Teflon FEP Fluoroplastic Film, 2013 (4 pages).
Product Information for DuPont Teflon PFA 340 Molding and Extrusion Resin, 2013 (2 pages).
Product Information for DuPont Teflon PFA 345 Molding and Extrusion Resin, 2013 (2 pages).
Product Information for DuPont Teflon PFA Fluoroplastic Film, 2013 (3 pages).
Sedev et al., "Wettability and surface energetics of rough fluoropolymer surfaces," *J Adhesion.* 80:497-520 (2004).
Communication Pursuant to Article 94(3) EPC for European Patent Application No. 11711614. 5-1408, dated Jul. 18, 2014 (6 pages).

* cited by examiner (b)

(c)

Antibody IgG-AP
Antibody in sample
Antigen
Surface

Antigens
A – PBS buffer
B – mouse IgG
C – FLAG peptide
D – Hepatitis B core Ag

Samples
1 – Buffer
2 – Anti-HB CAg
3 – Anti-FLAG

A – PBS buffer   C – FLAG peptide
B – mouse IgG    D – Hepatitis B core Ag

|   | Buffer | Anti-HB CAg | Anti-FLAG |
|---|--------|-------------|-----------|
| A | -      | -           | -         |
| B | +      | +           | +         |
| A | -      | -           | -         |
| B | +      | +           | +         |
| C | -      | +           | -         |
| D | -      | -           | +         |
| C | -      | +           | -         |
| D | -      | -           | +         |
| C | -      | +           | +/-       |
| D | -      | -           | +         |

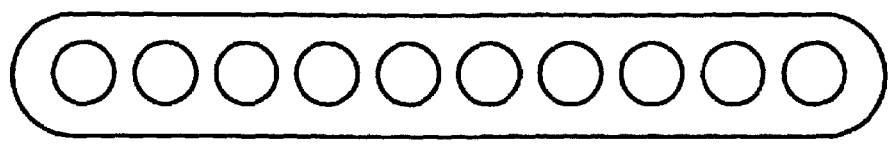
Fig. 26
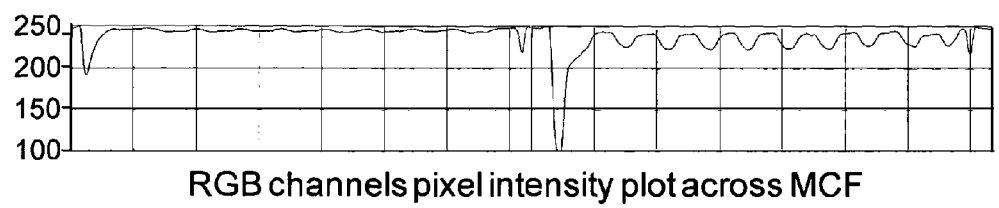
RGB channels pixel intensity plot across MCF
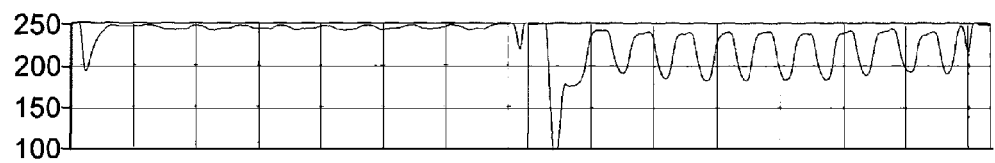
Blue channel pixel intensity plot across MCF
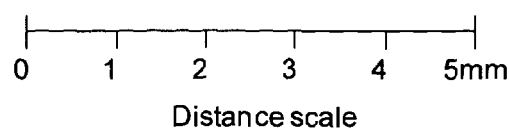
Distance scale
Fig. 27

Antibody IgG-HRP

Antibody HB Cag in sample

Anti-HB CAg

Surface

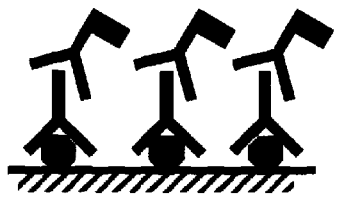

Fig. 30A

⦿⦿⦿⦿⦿⦿⦿⦿ Cross section of individual MCF test strip to scale

Anti-HB CAg concentration tested in each MCF strip (ng/ml)

1,000 | 333 | 111 | 37 | 12 | 4 | 1.3 | 0

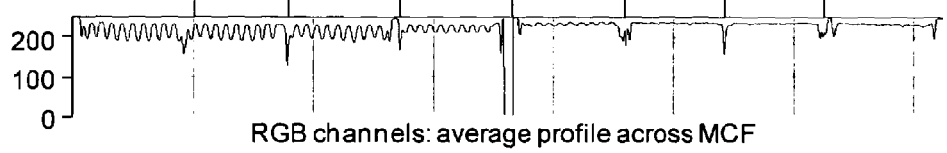

RGB channels: average profile across MCF

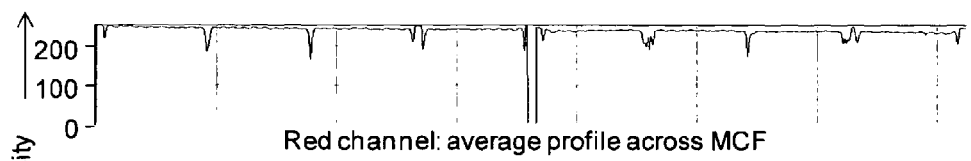

Red channel: average profile across MCF

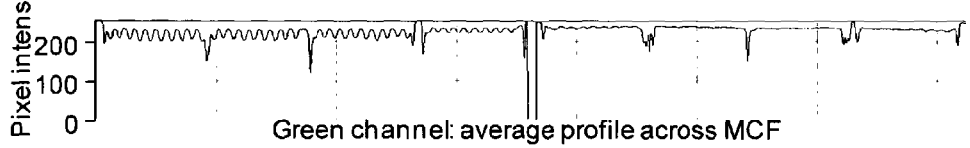

Green channel: average profile across MCF

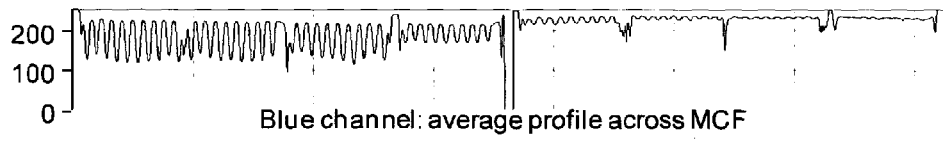

Blue channel: average profile across MCF

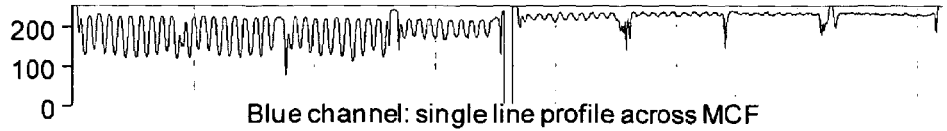

Blue channel: single line profile across MCF

Fig. 30B

|  | Time [min] | |
| --- | --- | --- |
| Step | 96 microwell | MCF-FEP |
| 1. Sample or standard | 120 | 10 |
| 2. Detection antibody | 120 | 10 |
| 3. Enzyme complex | 20 | 10 |
| 4. Colorimetric substrate | 25 | 20 |
| Total assay time | 285 | 50 |

IMMUNOASSAYS, METHODS FOR CARRYING OUT IMMUNOASSAYS, IMMUNOASSAY KITS AND METHOD FOR MANUFACTURING IMMUNOASSAY KITS

CROSS REFERENCE TO RELATED APPLICATIONS

This application is the U.S. National Stage of International Application No. PCT/GB2011/000414, filed Mar. 23, 2011, which claims benefit of United Kingdom Patent Application No. GB 1005191.0, filed Mar. 26, 2010, each of which is hereby incorporated by reference.

BACKGROUND TO THE INVENTION

1. Field of the Invention

The present invention relates to immunoassays, methods for carrying out immunoassays, immunoassay kits and methods for manufacturing immunoassay kits. In particular, the invention has relevance to capillary (especially microcapillary) immunoassay technology.

2. Related Art

Immunoassays (IAs) are powerful biochemical tools that allow measurement of the concentration of a substance in a clinical, medical, biotechnological or environmental sample. IAs normally utilise the specific interaction between antibodies and their antigens, and are used to measure biomolecules and small molecules in diverse applications including detection of pathogens, infection, drugs, disease biomarkers, environmental contaminants, biowarfare agents and toxins in food products. Heterogenous IAs work by immobilising an antigen or capture antibody onto, e.g., a plastic surface. The presence of an antigen or antibody in a sample can then be determined by a variety of methods, the most common being to label either antigen or the antibody. Common labels include enzymes, as used in enzyme-linked immunosorbent assay (ELISA). Other labels include colloidal gold (as used in lateral flow assays), radioisotopes such as I-125 as used in radioimmunoassay (RIA), magnetic labels as used in magnetic immunoassay (MIA) and fluorescent labels.

The most common platform for IA in life sciences laboratories are microtitre plates. The experimental procedure for a microtitre plate IA typically starts with coating the microwell surfaces (over an extended period of time, e.g. overnight) with the antigen or capture antibody, followed by vigorous washing. The samples are then added to the wells and incubated for a defined time, typically 2-8 hours for maximum sensitivity. Detection antibodies are then added to the wells after another extensive washing and incubated for more than 1 h. This results in a tedious, long procedure and high consumption of expensive reagents (the minimum operational volumes for 96-well microtitre plate wells are 50-100 µl). Specialised equipment for signal detection (e.g. a microplate reader) is also required, representing an investment cost of up to £20,000.

To address the problems of prolonged incubation times and high consumption of expensive reagents typical of microtitre plate based assays, alternative IA techniques have been developed which use plastic surfaces having a large surface area to volume, such as of the type shown by microbeads or microfluidics devices instead of microtitre plates.

Fluorescent or magnetic microbeads offer a very high specific surface area for the immobilization of antigen or capture antibody and can effectively be multiplexed or automated by means of a robotic system and a flow cytometer for signal detection. Nevertheless, to set up a microbead-based IA normally requires an investment of £50,000-100,000.

IA microbeads offer a very high specific surface area for the immobilization of antigen or capture antibody. Microbead IA offer advantages over microtitre plate IA being more suited to automation by means of a robotic system. A further advantage is the possibility of multiplex analyte measurement whereby one sample is analysed for multiple analytes simultaneously. Specialised equipment is required to detect the signal generated by microbead IA, such as a flow cytometer or a microbead analyzer for signal detection. Therefore the equipment required to set up a microbead-based IA normally requires an investment of £30,000-100,000.

In addition, some recent microfluidic technologies offer the possibility of processing multiple samples via automation, requiring minimum volumes of sample. Various types of microfluidic IA technologies are reviewed in Bange et al 2005.

Yacoub-George et al 2007 disclose a microfluidic apparatus for carrying out immunoassays. Their apparatus includes 10 fused silica capillaries held in a specially-designed cartridge. The cartridge is coupled to microfluidic pumps for individual control of the fluid type and fluid flow provided to each capillary. Different capillary elements have different antibodies immobilised at the internal bore surface. The apparatus also includes a specially-designed light-sensing detector module for measuring the immunoassay results from the capillaries.

However, for many applications, the cost of producing microfluidic devices e.g. by soft lithography with integrated signal detectors remains too high to be cost effective for IAs performed in many life sciences, clinical diagnostic, or other laboratories.

Other known types of IAs employ capillary elements, see for example U.S. Pat. No. 5,624,850. In these assays, the bore of the capillary providing a fluid conduit for a sample and antigen proteins or antibodies being immobilised at the internal surface of the bore of the capillary. Capillary-based IAs provide an advantage in terms of the available surface area of the capillary bore compared with the volume of sample required for microtitre plate based IAs. In addition, the high surface to volume ratios of capillaries compared with microtitre plates means that the length of the incubation times required for e.g. antigen-antibody binding are shortened.

A number of apparatuses for performing capillary-based IAs have been described. For example, U.S. Pat. No. 4,116,638 discloses a device for carrying out IAs using multiple capillaries simultaneously. The device comprises a vial with a circular disc inserted into the vial and openings in the disc into which capillaries can be inserted. In addition, the disc has a larger opening in its centre into which a tube can be inserted. This tube can be used to add e.g. samples to the vial which are then taken up by the capillaries.

Another apparatus for capillary-based immunoassays is described in U.S. Pat. No. 4,883,760. In one example, one or more capillaries are held in a flexible support structure and are initially suspended with their lower ends free. Samples etc. are introduced into the capillaries through an aperture in the support. The capillaries can then be drained by deflecting the upper part of the support downwards until the lower ends of the capillaries touch an absorbent material positioned below them.

U.S. Pat. No. 5,976,896 and U.S. Pat. No. 6,517,778 also describe an apparatus for capillary-based immunoassays. In one example, a cartridge comprising four capillary tubes is used to screen for different analytes in a milk sample. Three of the four capillaries in the cartridge were each coated with a different reagent thereby allowing detection of different analytes in a competitive immunoassay. The fourth capillary was left blank and acted as a control.

U.S. Pat. No. 4,590,157 discloses, in one embodiment, a device formed by connecting several capillary elements in series. Each capillary element is formed of a transparent material. Suitable examples given are glass, polyvinyl chloride or polystyrene. Each capillary element has a length of about 2 cm, an internal bore diameter of about 1 mm and an external diameter of about 2 mm. Each capillary element has different antibodies, antigens or haptenic substances adsorbed or covalently bonded at the surface of the bore. In use, a sample fluid is drawn through the series of capillary elements. The type of immunoassay performed is typically an enzyme-linked immunosorbent assay (ELISA). In an alternative embodiment, three capillary elements are arranged in parallel, each capillary tube being capable of indicating the presence of an analyte (digoxin) within different predetermined concentration ranges. In this way, a quantitative assay is provided. The unknown sample is draw through the parallel capillary elements by aspiration by three corresponding plungers. In each embodiment, the results of the assay are determined by an assessment of the colour change associated with each capillary element. A similar disclosure is provided by Healey et al, 1983.

Different methods for detecting signals produced in capillary-based IAs have also been described. For example, U.S. Pat. No. 4,716,121 describes a capillary-based fluorescent immunoassay in which an optical fibre is inserted into the capillary. Illumination of the fibre results in an evanescent wave being produced in the sample within the capillary which in turn excites fluorescently-tagged complexes. The resulting fluorescence then enters the fibre and is collected by a fluorimeter.

Capillaries have also been used as measuring devices in immunoassays. For example, U.S. Pat. No. 4,454,235 describes an apparatus for performing immunoassays in which a capillary is used to transfer a precise amount from a first container containing a mixture of sample and fluorogenic agent to a second container containing a second reagent. The capillary tube in this case is held within a support so that at least one end of the capillary is accessible to fluid. Once the mixture has been transferred to the second container, fluorescence is measured by placing the second container in a fluorometer.

Another system for carrying out IAs is described in U.S. Pat. No. 6,340,598. In this system a biosensor comprising a planar waveguide is used to detect the presence of an analyte in a sample. The waveguide in this case forms at least one wall of the sample reservoir and a light source is position to focus light into the waveguide, wherein internal reflection within the waveguide leads to the production of evanescent light. The apparatus further has a detector for detecting fluorescence emitted by tracer molecules in a test solution in response to stimulation with evanescent light.

SUMMARY OF THE INVENTION

The present inventors note that there are disadvantages associated with practical available immunoassay technologies. In particular, known IA technologies require the use of relatively large volumes of reagent, and/or require dedicated complex readers for carrying out IA measurements, and/or are not easily susceptible of mass production.

Accordingly, the present inventors have devised the present invention in order to address one or more of these disadvantages.

As discussed above, many types of immunoassay rely on optical interrogation to determine the progress and/or outcome of the immunoassay. The present inventors have realised that one barrier to addressing one or more of the disadvantages outlined above using capillary-based immunoassay devices is that it can be difficult reliably to interrogate the capillary bores, particularly where a quantitative result is required from the immunoassay. This is particularly the case where it is wanted to carry out immunoassays in multiple capillary bores substantially simultaneously, e.g. to provide redundancy in the results or to provide different immunoassays in different capillary bores.

Accordingly, in a first preferred aspect of the invention, there is provided a device for carrying out an immunoassay, the device having:

a unitary body with an exterior surface, and
at least two capillary bores extending internally along the unitary body, wherein for each capillary bore a population of first members of a respective specific binding pair is immobilised at least at a portion of the surface of the capillary bore, each first member being capable of specifically binding with a second member of the respective specific binding pair,
wherein the unitary body is substantially transparent to visible light to allow optical interrogation of the capillary bores.

The present inventors have realised it can be difficult reliably to interrogate capillary bores known for use in immunoassay techniques, particularly where a quantitative result is required from the immunoassay. The inventors have realised that this is due primarily to adverse optical effects. For example, when viewing a capillary bore from one direction, the light from close to the lateral sides of the bore tends to be subject to a greater degree of refraction than the light from the centre of the bore.

The optical signal to be optically interrogated is generated during the IA to determine the level of analyte in the sample, and this almost always takes place in an aqueous solution/suspension. The inventors have therefore realised that forming an immunoassay capillary device from a material having a refractive index close to that of water allows the adverse optical effects mentioned above to be avoided to the extent that allows a significant improvement in optical interrogation of the capillary bore. The refractive index of water is 1.33 (when measured at 20° C. with light of wavelength 589 nm, corresponding to the yellow doublet sodium D line). For reference, it is of interest to provide here the refractive index of some other materials under the same conditions: fused silica 1.46; poly (ether urethane) 1.49; poly (methyl methacrylate) 1.49; poly (vinyl alcohol) 1.50; polyethylene 1.51; low density polyethylene 1.51; polyethylene terephatalate 1.57-1.58; polystyrene 1.59; poly (vinyl chloride) 1.54.

Accordingly, it is preferred that the immunoassay device is formed from a material having a refractive index which is within plus or minus 0.07 of the refractive index of the sample fluid. Preferably, the refractive index is measured at 20° C. with light of wavelength 589 nm.

Preferably, the unitary body is formed of a material having a refractive index in the range 1.26 to 1.40, the refractive index being measured at 20° C. with light of wavelength 589 nm. This is suitable, for example. where the sample fluid is dilute and aqueous.

It is noted here that this refractive index feature itself may stand as an independent aspect of the present invention.

Accordingly, in one aspect, the present invention provides a device for carrying out an immunoassay, the device having:
a unitary body with an exterior surface, and
at least one capillary bore extending internally along the unitary body, wherein for each capillary bore a population of first members of a respective specific binding pair is immobilised at least at a portion of the surface of the capillary bore, each first member being capable of specifically binding with a second member of the respective specific binding pair,
wherein the unitary body is substantially transparent to visible light to allow optical interrogation of the capillary bore, and wherein the unitary body is formed of a material having a refractive index which is within plus or minus 0.07 of the refractive index of the sample fluid, the refractive index being measured at 20° C. with light of wavelength 589 nm.

In another aspect, the present invention provides a method of performing an immunoassay for detecting the presence or absence of the second binding member in a sample fluid using a device according to the first aspect, the method including the steps:
providing a sample fluid in the capillary bores of the device; and optically interrogating the capillary bores.

Preferably, the method comprises incubating the sample fluid with the population of first members of the specific binding pair for 20 minutes or less, more preferably for 15 minutes or less, most preferably for 10 minutes or less. For example, the sample fluid may be incubated with the population of first members for 10 to 20 minutes, more preferably for 10 to 15 minutes, most preferably for about 10 minutes.

The present inventors have also realised that the manufacture of a capillary-based immunoassay device can be difficult to carry out on a relatively large scale. Accordingly, the inventors have devised a manufacturing method that allows the production of capillary immunoassay devices pre-loaded with populations of first members of respective specific binding pairs for specifically binding with second members of the respective specific binding pairs. The inventors have realised that it is possible to load the first members of a specific binding pair into a long length of a capillary body (e.g. 20 cm or longer), the capillary body subsequently being cut to the desired length for an immunoassay device. In general terms, the body may include one capillary bore, but this is not preferred.

Accordingly, in another aspect, the present invention provides a method for manufacturing a device according to the first aspect, the method including:
providing an extruded body having at least two capillary bores extending internally along the body; and
inserting a respective loading fluid into each capillary bore of the extruded body, each loading fluid comprising said first members of the respective specific binding pair, to immobilise the first members at least at a portion of the surface of the capillary bore and forming a loaded extruded body.

Preferably, the method further includes the step of cutting the loaded extruded body to form the device for an immunoassay of a required length, wherein the loaded extruded body, before cutting, optionally has a length of at least 20 cm.

Alternatively, the method may be a method for manufacturing a set of n devices, the method further including cutting the loaded extruded body to form the set of n devices, each device having a length of at least X, wherein the loaded extruded body, before cutting, has a length of at least nX, or a length of at least 20 cm.

In another aspect, the present invention provides an immunoassay system for carrying out immunoassays, the system having a plurality of immunoassay devices according to the first aspect, and a holder for holding the plurality of immunoassay devices.

In a still further aspect, the present invention provides an immunoassay kit including an extruded body having at least two capillary bores extending internally along the body, the extruded body having a length of at least 20 cm, a population of first members of a respective specific binding pair being immobilised at the surface of each capillary bore, each first member being capable of specifically binding with a second member of the respective specific binding pair, the extruded body being capable of being cut to a required length for an immunoassay.

The kit may be provided in the form of a reel of the loaded extruded body.

Further preferred (or at least optional) features are set out below. Unless the context demands otherwise, these can be combined either singly or in any combination with any aspect of the invention. Similarly, any aspect of the invention can be combined with any other aspect of the invention.

The capillary bore may have an inner diameter of at least 10 µm. Preferably, the inner diameter is at least 50 µm. The inner diameter may be up to 1 mm. More preferably, the inner diameter is about 200 µm. The cross sectional shape of the capillary bore may be circular. However, more preferably it is oval, in view of the preferred manufacturing technique for the device. In that case, the "inner diameter" is to be taken as the maximum width of the capillary bore in cross section.

The device may have more than two capillary bores formed in the unitary body. For example, the device may have 3, 4, 5, 6, 7, 8, 9, 10 or more capillary bores. It is possible to manufacture a suitable device with 20 capillary bores, or more.

Preferably, the capillary bores are formed substantially parallel to each other.

Preferably, one capillary bore in the device has a differently-treated surface from at least one other capillary bore in the device. This may provide a measurable difference in immunoassay performance between the bores. For example, one bore may have a different concentration of first members adsorbed at its surface than another bore. Additionally or alternatively, one bore may have been treated with first members of a different specific binding pair compared with another bore. In some embodiments, at least one reference capillary bore may be provided without said first members adsorbed at the surface of the capillary bore. Furthermore, it is possible for two or more capillary bores to receive identical treatment, in order to provide measurement redundancy in the device. Still further, it is possible for two or more capillary bores to receive identical treatment and for one or more other bores in the same device to receive different treatment, to provide combinations of these advantages.

Where the device comprises two or more capillary bores, one or more of the capillary bore(s) may be detached from one or both of its neighbouring capillary bores at one end of the device. For example, each capillary bore in the device may be detached from every other capillary bore at one end of the device. Alternatively, the capillary bores may be divided into sets of capillary bores and each set of capillary bores may be detached from every other set of capillary bores at one end of the device. Each set may comprise two or more, e.g. 2, 3, 4, 5, 6, 7, 8, 9, or 10 capillary bores. "Detached" in this context means that at one end of the device, the capillary bore or set of capillary bores is not attached to one or both of its neighbouring capillary bore(s) or set(s) of capillary bores.

A method for manufacturing a device according to the present invention may thus comprise a step of separating or detaching the capillary bores or sets of capillary bores from each other at one end of the device, e.g. by cutting the device between the capillary bores. Separation of the capillary bores or sets of capillary bores at one end of the device facilitates contacting each capillary bore or set of capillary bores with different sample fluid when the device is used to perform an immunoassay.

The capillary bores or sets of capillary bores may have identically treated surfaces. Alternatively, one capillary bore in each set of capillary bores in the device may have a differently-treated surface from at least one other capillary bore in the same set of capillary bores. This may provide a measurable difference in immunoassay performance between the bores of the set. For example, one bore may have a different concentration of first members adsorbed at its surface that another bore in the same set of bores. Additionally or alternatively, one bore may have been treated with first members of a different specific binding pair compared with another bore in the same set of bores. In some embodiments, at least one reference capillary bore may be provided without said first members adsorbed at the surface of the capillary bore in each set of capillary bores. Furthermore, it is possible for two or more capillary bores in each set of capillary bores to receive identical treatment, in order to provide measurement redundancy in the device. Still further, it is possible for two or more capillary bores in each set of capillary bores to receive identical treatment and for one or more other bores in the same set to receive different treatment, to provide combinations of these advantages. Preferably, the sets of capillary bores in the device are duplicates of each other, i.e. the bores in one set of capillary bores are treated with the same first member or members as the bores of other sets in the same device. This allows the same immunoassay to be preformed on several fluid samples simultaneously.

Preferably, the exterior surface of the body includes a measurement first surface and a measurement second surface. In use, it is intended that light will be transmitted through the device from the measurement first surface to the measurement second surface. These surfaces may, for example, be upper and lower major surfaces of the body. Preferably one or both of the measurement first surface and the measurement second surface extend substantially parallel with the principal axes of the capillaries. One or both of the measurement first surface and the measurement second surface may extend substantially parallel with the arrangement direction of the capillaries.

One or both of the measurement first surface and the measurement second surface may be substantially planar. The advantage of this is that optical distortions due to refraction at the measurement surfaces can be reduced or avoided. In turn, this can improve the signal-to-noise ratio of a measurement taken by optical interrogation of the capillary bore. Note that typically the body also includes side surfaces. The shape of the side surfaces is not considered to be critical, since preferably optical interrogation of the capillary bores does not take into account light from or close to the side surfaces.

Preferably, the body of the device is formed of a material having a refractive index in the range of plus or minus 0.05 of the refractive index of the sample fluid. For example, in the case where the sample fluid is aqueous, a preferred lower limit for the refractive index of the material of the body of the device is 1.28. A preferred upper limit for the refractive index of the material of the body of the device is 1.38. The refractive index is measured at 20° C. with light of wavelength 589 nm. Most preferably, the refractive index of the material of the body of the device is substantially identical to the refractive index of the sample fluid.

In addition to being substantially transparent to visible light, the material of the body of the device may also be substantially transparent to electromagnetic radiation in the invisible spectrum, e.g. ultraviolet (UV) light.

Preferably, the length of the extruded body, before cutting, is at least 50 cm. The length may be greater, e.g. at least 1 m, preferably at least 2 m, 3 m, 4 m, or 5 m. Most preferably the length of the extruded body, before cutting, is at least 5 m.

The immunoassay may be performed including an optical interrogation step. Preferably, this is performed to provide a pixellated image of one or more, or all, of the capillaries. For example, a digital camera may be used. However, more preferably, a flatbed scanner is used. Subsequently, the image may be processed to determine a numerically averaged value for pixel intensity corresponding to the (or each) capillary. This value may be used to ascribe measurement values to the immunoassay in the (or each respective) capillary.

Preferably, in the immunoassay system, the holder holds the immunoassay devices in a substantially planar array. Furthermore, preferably the holder provides observation means (such as an observation window) to allow at least a part of each immunoassay device to be observed. The observation means may also allow each immunoassay device to be optically interrogated for measurement.

The holder preferably also allows the immunoassay to proceed whilst the immunoassay devices are held in the holder.

The system may further include a tray having an arrangement of wells adapted to receive reagents, sample fluids or other liquids required for the immunoassay. The tray is preferably further adapted to receive at least an end of each immunoassay device when the immunoassay devices are held in the holder. This allows one end of each capillary bore to be in fluid communication with a liquid held in the respective well.

Preferably, the holder provides means for aspirating fluid through the capillary bores of the immunoassay device. Typically, the holder allows this aspiration to take place at the same time, e.g. using a single aspiration device such as a pipettor.

A sequence of fluids may be aspirated through each capillary by moving the holder along the tray to be in register with a corresponding sequence of wells containing respective fluids.

An IA, as referred to herein, is an assay for determining the presence (or measuring the concentration) of a member of a specific binding pair in a sample, which makes use of the specific binding between said member and a second member of the specific binding pair. The term binding pair refers to a first member and a second member which are capable of specifically binding with one another. Examples of binding pairs are antigen-antibody, biotin-avidin, hormone-hormone receptor, receptor-ligand, and enzyme-substrate. The present invention is in particular concerned with antigen-antibody type binding pairs.

When an IA is performed in a device according to the first or second aspect, the incubation time required for the various reagents is reduced compared with IAs performed in e.g. 96 microwell plates using the same concentrations of reagents.

For example, where the presence (or concentration) of a second member of the specific binding pair in a sample is measured, the sample may be incubated with the population of first members for 20 minutes or less, for 15 minutes or less, or for 10 minutes or less. For example, the sample fluid may be incubated with the population of first members for 10 to 20 minutes, for 10 to 15 minutes, or for about 10 minutes.

Many different types IAs are known in the art, including non-competitive and competitive IAs. Some examples are briefly described below.

Non-competitive IAs may involve, for example, immobilising an antibody capable of specifically binding with an antigen at a solid support. The immobilised antibody may then be brought into contact with a sample of interest. If the sample contains the antigen in question, it will bind with the antibody. A second antibody, which is also capable of binding with the antigen but which binds to a different epitope on the antigen than the first antibody, is then added and allowed to bind. To allow detection, the second antibody may be labelled with a detectable label. Alternatively, a third antibody known to be capable of specifically binding with the second antibody and labelled with a detectable label may be added and allowed to bind to the second antibody. The amount of labelled antibody bound to the solid support is then measured, whereby the amount of labelled antibody detected is directly proportional to the amount of antigen present in the sample. FIGS. 8, 9 and 10 show schematic examples of non-competitive IAs.

As already described above in relation to the sample fluid, the incubation times for the second (and third antibody, if present) are similarly reduced in IAs performed in devices according to the first or second aspect compared with IAs performed in e.g. 96 microwell plates using the same antibody concentrations. Specifically, the second and/or third antibody may be incubated in the capillary bore(s) for 20 minutes or less, for 15 minutes or less, or for 10 minutes or less. For example, second and/or third antibody may be incubated in the capillary bore(s) for 10 to 20 minutes, for 10 to 15 minutes, or for about 10 minutes.

Competitive IAs may involve immobilising, for example, an antibody or an antigen at a solid support depending on whether the assay is intended to determine the presence of an antigen or an antibody in a sample of interest. For example, where it is intended to assay for the presence of an antigen in a sample, an antibody which is capable of specifically binding with said antigen may be immobilized on a solid support. Labelled antigen is then added and allowed to bind to the immobilized antibody, followed by addition of the sample. If the sample contains the antigen in question, it will compete with the labelled antigen for binding to the immobilized antibody. The amount of labelled antigen bound to the solid support is then measured. In this case the amount of labelled antigen detected is inversely proportional to the amount of antigen present in the sample.

A first member of a specific binding pair is capable of specifically binding with a second member of a specific binding pair. A first member of a specific binding pair may, for example, be a protein (e.g. an antibody), a polysaccharide, a peptide, a nucleic acid, or small molecule (e.g. a hapten). A second member of a specific binding pair may similarly be a protein (e.g. an antibody), peptide, nucleic acid, or small molecule (e.g. a hapten). A second binding member may be comprised in an analyte.

Where the specific binding pair is an antibody-antigen binding pair, the first binding member may, for example, be an antibody and the second binding member may be an antigen, wherein the antibody is capable of specifically binding with the antigen. Alternatively, the first binding member may be an antigen and the second binding member be an antibody, wherein the antigen is capable of specifically binding with the antibody.

The first member of the specific binding pair can be immobilised to the solid support in a number of different ways known in the art. For example, the first member of a specific binding pair may be adsorbed directly to the solid support, e.g. through electrostatic and/or hydrophobic interactions, such as in the case of plastic solid supports. Alternatively, the first member of the specific binding pair can be covalently attached to the solid support. In this case, the solid support may be chemically modified to introduce or activate functional chemical groups on the surface of the support, such as hydroxyl or amine groups, and the support crosslinked using crosslinking agents such as gluteraldehyde, to facilitate covalent binding of the first member to the solid support. In a further alternative, the first member of the specific binding pair can be indirectly attached to the solid support by a specific binding interaction, for example by an interaction between biotin and avidin, or by immobilising protein A or protein G to the solid support followed by specific binding to antibody molecules.

The term "antibody" describes an immunoglobulin whether natural or partly or wholly synthetically produced. The term also covers any polypeptide or protein comprising an antibody antigen-binding site. Thus, this term covers antibody fragments, derivatives, and chimeric molecules comprising an antibody antigen-binding site, or equivalent, fused to another polypeptide (e.g. derived from another species or belonging to another antibody class or subclass).

Antibody fragments that comprise an antibody antigen-binding site include, but are not limited to, antibody molecules such as Fab, Fd, Fv, dAb, isolated CDR regions, F(ab')2, Fab', Fab'-SH, scFv, bispecific single chain Fv dimmers; and diabodies. Such antibody fragments are well known in the art.

An antigen-binding site as referred to herein is the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is referred to as an epitope. An antibody antigen-binding site may be provided by one or more antibody variable domains. An antibody antigen-binding site may comprise an antibody light chain variable region (VL) and an antibody heavy chain variable region (VH).

An antigen as referred to herein is any substance which can specifically bind with an antibody. Such substances include: proteins, peptides, polysaccharides, nucleic acids, and small molecules (e.g. haptens).

The terms "specific" and "specifically" as used herein may refer to the situation where one member of a specific binding pair will not show any significant binding to molecules other than its specific binding partner(s), e.g. the other member of the specific binding pair. These terms also apply where e.g. an antigen binding domain is specific for a particular epitope which is carried by a number of antigens, in which case the specific binding member carrying the antigen binding domain will be able to bind to the various antigens carrying the epitope.

Binding of a first binding member to a second binding member may be detected directly or indirectly.

Where binding of the first binding member to the second binding member is detected directly, the second binding member may be labelled with a detectable label. If a sample comprising second binding members is then added, these unlabeled second binding members will compete with the labelled second binding members for binding to the first binding member. In this case, the amount of label detected is inversely proportional to the amount of second binding member present in the sample.

Where binding of the first binding member to the second binding member is detected indirectly, binding may be detected by using a third binding member, e.g. an antibody, capable of specifically binding with the second binding member and labelled with a detectable label. Alternatively, binding of a first binding member to a second binding member may be detected by using a third binding member, e.g. an antibody, capable of specifically binding with the second binding member and a fourth binding member capable of specifically binding with the third binding member and labelled with a detectable label.

A detectable label as referred to herein may be any label which produces or can be induced to produce a signal, including but not limited to fluorescers, chemiluminescers (e.g. horseradish peroxidase), coloured labels (e.g. latex [blue] or colloidal gold [red]), radiolabels, enzymes, and magnetic labels. The amount of label bound at a surface, e.g. a surface of a capillary bore, may therefore be detected and/or measured by detecting fluorescence or luminescence, colour, radioactivity, enzyme activity, or changes in magnetic field. Detectable labels may be attached to binding members using conventional chemistry. Preferably, a detectable label is a label detectable by optical interrogation, e.g. with a digital camera or flatbed scanner. Labels that can be detected by optical interrogation include fluorescers, chemiluminescers and coloured labels. The mechanism by which a signal can be generated for optical detection includes (but is not necessarily limited to): light absorption, light scattering, light diffraction, light reflection, fluorescence or luminescence.

The term "comprise" is generally used herein in the sense of include, i.e. permitting the presence of one or more additional features or components.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described below.

BRIEF DESCRIPTION OF THE DRAWINGS

FIGS. 6 and 7 show the direct impact in diffusion distance provided by practical lengths of capillaries (in the range 5-50 mm), compared to standard microtitre plate wells.

FIG. 24A shows a schematic representation of antibody adsorption and detection in the MCF-FEP.

FIG. 24B shows a plot of mean fluorescent intensity across the capillary array. The mouse IgG concentrations (µg/ml) in each capillary are indicated below the plot.

FIG. 24c shows a plot of height, h, of grey fluorescent intensity measured at the inlet and outlet of a 5 meter reel of MCF.

FIG. 26 shows a schematic view of a cross section of the format of an immunoassay device used to obtain the results shown in FIG. 27.

FIG. 27 shows images obtained from scanning an immunoassay device according to the present invention using a flatbed scanner after an immunoassay.

FIGS. 30A, 30B, 31 and 32 demonstrate the sensitivity of the preferred embodiment of the present invention in comparison to a microtitre plate for a Hepatitis B detection assay.

FIG. 30A shows a schematic representation of the performed enzyme-linked immunosorbent assay in the MCF-FEP FIG. 30B shows the average light intensity measured by scanning 8 different individual strips of MCF-FEP in which an immunoassay to detect antibodies to Hepatitis B was performed to test 8 different concentrations of anti-hepatitis B core antigen antibody. The average light intensity is plotted against the distance across the MCF-FEP strips, with the concentration of antibody in each sample indicated above the plots. The average light intensity was calculated for a length of approximately 1 mm measured parallel to the axis of the capillary.

FIG. 31 shows a plot of mean peak intensity for all samples against concentration of anti-HB-CAg.

In FIG. 39 the capillaries are individualized, allowing each capillary to be brought into contact with a different sample tray. Alternatively, the capillaries may be separated into pairs of two capillaries each, as shown in FIG. 40. The two capillaries can then receive identical treatment to provide measurement redundancy in the device. Separating the capillaries into other arrangements e.g. sets of three capillaries or more is also envisaged. The separation can be varied depending on the number of samples to be analyzed, the number of controls required and whether measurement redundancy is to be provided in the device.

Figure 1:
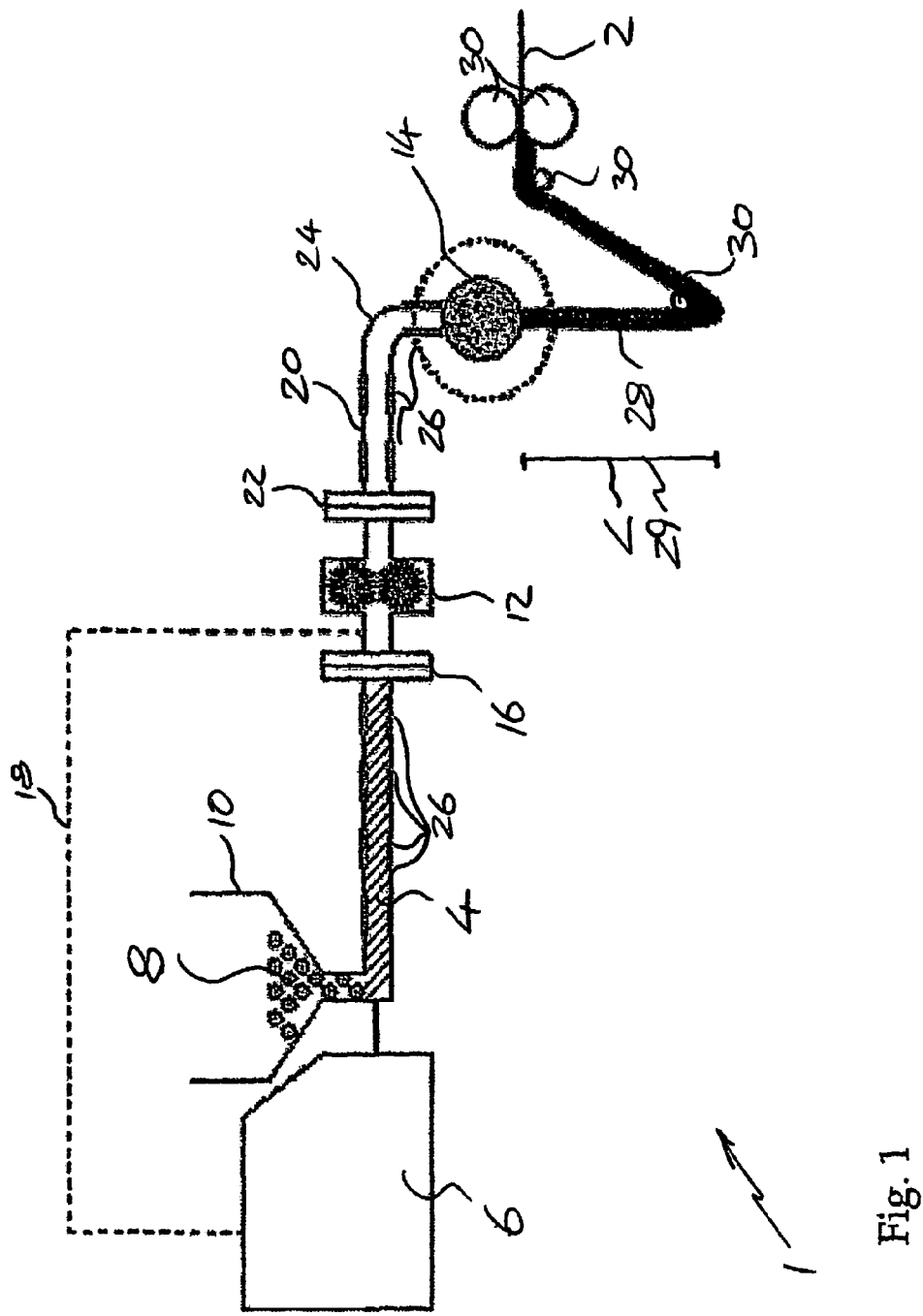
FIG. 1 is a schematic diagram of an extrusion apparatus for use in manufacturing immunoassay devices according to a preferred embodiment of the invention.

DETAILED DESCRIPTION OF THE PREFERRED EMBODIMENTS, AND FURTHER PREFERRED FEATURES OF THE INVENTION

In a preferred embodiment of the present invention, there is provided a platform for multiplexed quantitative immunoassays (IAs). The present inventors have shown that antigen proteins and antibodies can be successfully immobilised at the super-hydrophobic inner surface of an array of 10 microcapillaries having an internal diameter of about 200 µm and embedded in a single substantially flat plastic film extruded from a fluoropolymer material. Short sections of the plastic film (up to 5 cm long) have been interfaced with a standard micropipettor allowing multiple analytes detection with a single sample feeding port and using minimum volume of reagents. The flat geometry and excellent optical properties of the plastic film allows direct cross-interrogation of the capillaries for signal detection and quantification using conventional optical systems, such as a CCD camera or a flatbed scanner. The small internal volume and diameter of the capillaries allows significant reductions in reagent costs and time of assay in comparison with the microtitre plate IAs. Furthermore, the investment costs related with the acquisition of specialised detection equipment can be minimised without affecting the sensitivity of the IA. This new multiplexed IA platform finds major application for example as a clinical diagnostic tool for the detection of cardiac and cancer diseases in developed countries or pathogens detection in third world countries.

In a preferred embodiment, the present invention utilises a capillary body manufactured in accordance with the disclosure of WO 2005/056272, the content of which is hereby incorporated by reference in its entirety.

WO 2005/056272 discloses apparatus for producing an extrudate product, the extrudate product including a plurality of capillary channels therethrough, the apparatus comprising an extruder having an inlet, a die including an orifice having a predetermined outer shape, a plurality of needles each having a body including an internal conduit for fluid flow, each needle further comprising an outlet from the internal conduit at an outlet end, the outlet end of each needle being arranged in a predetermined pattern substantially within the orifice of the die, the conduit of each needle being fluidly connected to a fluid source, wherein, in use:
a) extrudable material is fed into the extruder through the inlet;
b) the extruder forces the extrudable material around the bodies of the needles towards the die and through the orifice in the die to produce an extrudate product having substantially the predetermined outer shape;
c) the needles allow fluid to be drawn from the fluid source through the conduit to be entrained in the extrudate product to form capillaries such that the extrudate product includes capillaries therealong in the predetermined pattern.

It has been found that the problem of die swell within the capillary is substantially reduced or negated when fluid is allowed to enter the capillary. This allows the bore of the capillaries to be more accurately controlled so small bore capillaries can be reliably produced. It is envisaged that capillaries having a bore of between about 2 mm to 10 microns may be produced in a single stage of melt processing. However, it is envisaged that a further processing stage could produce capillaries having a bore of below 1 micron, It should be understood that the capillary bores are also referred to as micro-capillaries.

It is preferred that the needle outlets are substantially regularly distributed in the die orifice as this helps to prevent maldistribution of the extrudate. It is preferred that each needle outlet is a substantially equal distance from other outlets and from the orifice of the die. For example, if the die orifice is substantially rectangular and the predetermined pattern of needle outlets is a simple line of outlets within the orifice it is preferred that the line is arranged substantially centrally in the short side of the rectangle and that the distances between the needle outlets are substantially identical to the distance between the outer needle outlets and the short edges of the orifice, and the line of outlets and the long edges of the orifice. The needle outlet may be any suitable size, but it is preferably between 2 mm and 0.1 mm and most preferably between 0.6 mm and 0.2 mm. For instance, with a needle outlet size of 0.3 mm capillary bores of between 200 microns and 20 microns can be readily produced depending on the processing conditions.

It is preferred that the pressure of the fluid entering the capillaries through the needles is substantially equal to the pressure of the environment into which the extrudate product is being extruded as it has been found that this produces a more stable extrudate product. It is preferred that the flow of extrudable material entrains the fluid in the capillary, but it should be understood that the fluid may enter the capillaries at above or below the pressure of the environment into which the extrudate product is being extruded, but that greater control may be needed. The fluid allowed to enter the capillaries will typically be air at room temperature and pressure, but the extrusion may be in a liquid bath or other non-typical environment. The fluid source may be air at room temperature and pressure if the extrudate product is being extruded into such an environment and can be drawn straight from the local atmosphere. However, it should be understood that the fluid source may be an inert gas or liquid, or a sample gas or liquid that is to be trapped within the capillaries in the extrudate product.

It is preferred that a gear pump is used to steady the flow of extrudable material between the extruder and the die. This helps to reduce any flow abnormalities that may result from variations in the operation of the extruder.

The die is used to take the feed of material from the extruder and change the shape of the material flow until it has the desired outer shape and can exit though the die orifice which has substantially the predetermined outer shape. It should be understood that, due to die swell, the outer shape of the extrudate may not correspond exactly with the predetermined shape of the orifice. It is preferred that the die is a converging die. The die is preferably shaped to ensure that the flow over the needles is substantially even as this helps to create a well formed, regular extrudate.

It is preferred that the die orifice is substantially rectangular so the resulting outer shape of the extrudate product is substantially rectangular. The dimensions of the rectangular orifice are preferably such that the extrudate product is a sheet or film. Preferably the rectangular orifice has a long side having a length that is at least times longer than the short side. Preferably the ratio is greater than 10 as this may allow the film to flex more readily. It should be understood that the orifice could take any other suitable shape, including an annulus, square or circle. It has been noted that with a non-circular die, for instance a rectangular die there may be edge effects that alter the shape of the capillaries at or near an edge of the film. Such edge effect may be negated through the use of an annular die which is, in effect, a continuous film having no edges. An annular die may allow the production of an extrudate product have greater consistency in the size and shape of the capillaries.

For simplicity the apparatus will now be described with reference to a preferred embodiment in which the die has a substantially rectangular orifice in which an array of needle outlets are arranged in a line substantially parallel with the long side of the rectangle and substantially in the centre of the short sides of the orifice. This produces an extruded film having a plurality of capillaries therealong. It should be understood that different arrays and orifice shapes could be employed.

It is preferred that the needle outlets are substantially circular in shape. This shape of outlet is easy to form, but other shapes could be used if desired. It is also preferred that the body of each needle is substantially cylindrical and is elongate along a first axis. The bodies are preferably arranged such that the first axis of the cylindrical body is substantially parallel with the flow of material as this provides a low resistance to the material flow and is simple to manufacture.

It should be understood that the plurality of needles may be formed individually, integrally, or in groups of two or more needles. For example a solid monolith of metal could be used to form a plurality of needles. The monolith may include holes therethrough to form the needles required by the invention. The needles may include a common inlet which then divides into a plurality of conduits leading to a plurality of outlets. The outlets of the needles from the monolith may protrude from the monolith allowing the extrudate to flow around the protrusion before gas is drawn from the outlet, or there may be no protrusion. The extrudate will flow around the monolith and draw gas through the outlets as described above.

Although it has been mentioned above that die swell within the capillaries is substantially reduced or negated, die swell still occurs at the die exit. The outer shape of the extrudate product will swell as it exits the orifice. In the case of the film, it has been found that the swell is greater along the short axis of the rectangular orifice than along the long axis. The result is that the substantially circular capillaries within the extrudate prior to swelling are distorted into an elliptical shape with the long axis substantially parallel to the short axis of the rectangular cross section of the film. It should be understood that with variations in outlet shape and processing, the capillaries cross section can be varied.

The extrudate product is preferably drawn away from the orifice at a rate greater than the rate at which the product is produced. The draw ratio is the ratio of the rate of production of extrudate to the rate at which the extruded product is drawn off. At some draw ratios (between 16 and 20) it appears that the die swell effect dominates and the capillaries are substantially elliptical.

At higher draw ratios (above 30) the change in geometry due to the extrudate drawing dominates. As has been shown in the literature, during drawing of an extrudate having a rectangular cross section, the length of the short axis decreases at a faster rate than the length of the long axis of the extrudate and so the capillaries are distorted to form substantially elliptical capillaries that have their long axis substantially parallel to the long axis of the rectangular cross section. The drawing process typically reduces the overall cross sectional dimensions of the extrudate product and therefore reduces the dimensions of the capillaries within the product.

It has also been found that it may be possible to further process the extrudate product after drawing. This further processing can be either cold drawing or warm drawing at an elevated temperature. It has been found that cold drawing can reduce the product dimensions by between two and three times and a greater reduction is to be expected when warm drawing is used.

The apparatus and a process using the apparatus is capable of producing rectangular section extrudate product with multiple capillaries running along the length of the product.

WO 2005/056272 discloses the production of extrudates with elliptical multiple capillaries of major axis length roughly 65 µm and minor axis length of about 35 µm. It should be noted that the aspect ratio and the mean diameter of the capillary can be varied through changes in the process conditions. The extruded products typically take the form of films. Each film typically has a length and a substantially rectangular cross section perpendicular to said length, said cross section including two long sides and two short sides, the film including a plurality of capillary bores substantially parallel to the length of the film.

WO 2005/056272 further discloses that the production of a length of extrudate of about 20 m long allowed an investigation of the dimensions of the capillaries at five sections along the extrudate via scanning electron microscopy. This revealed that the variation in the dimensions of the capillaries was no greater than about 10% along the length of the product.

WO 2005/056272 still further discloses the formation of extruded products using, for example LLDPE. Such polymers are found to have good optical transparency, despite any crystalline content present within the polymer. WO 2005/056272 suggests that total, or at least a significantly increased level of, optical transparency could be achieved by using an amorphous polymer such as polystyrene. However, it is to be noted that these materials are not necessarily the preferred materials for use with the embodiments of the present invention.

FIG. 1 shows extrusion apparatus 1 for creating an extrudate product 2 having capillary bores therealong. The extrusion apparatus comprises screw extruder 4 driven by a motor 6. Extrudable material 8 is fed to the extruder screw 4 through a hopper 10. As the extrudable material passes through the extruder screw 4 the material is melted to form a melt (not shown). The extruder screw 4 feeds the melt to a gear pump 12 which maintains a substantially constant flow of melt towards a die 14. The gear pump 12 is connected to the extruder screw 4 by a flange 16 which includes a screen filter to remove impurities from the melt flow. The motor 6 is controlled using a pressure feedback link 18 between the inlet of the gear pump and the motor 6.

The melt passes to the die 14 through an extruder barrel 20 which is connected to the gear pump by a flange 22. In this embodiment the extruder barrel includes a 90° bend 24. Band heaters 26 are used to control the temperature at different stages in the extrusion apparatus 1. Band heaters 26 may be located within the extruder, on the flanges 16,22, on the gear pump 12, on the extruder barrel 5 20 and also on the die 14.

The detail of the arrangement of the die 14 will be shown in greater detail in subsequent figures.

The melt passes through the die 14 and is formed into the desired shape and cross section. As the melt passes out of the die it becomes an extrudate 28. The extrudate 28 is drawn down over and between rollers 30. The drawing down process, as described above, alters the cross section of the extrudate 28 to form the extrudate product 2. A draw length (L) 29 is defined between the orifice and the first roller 30. It has been found that L has a great effect on the extrudate product 2 formed by this apparatus.

Figure 2:
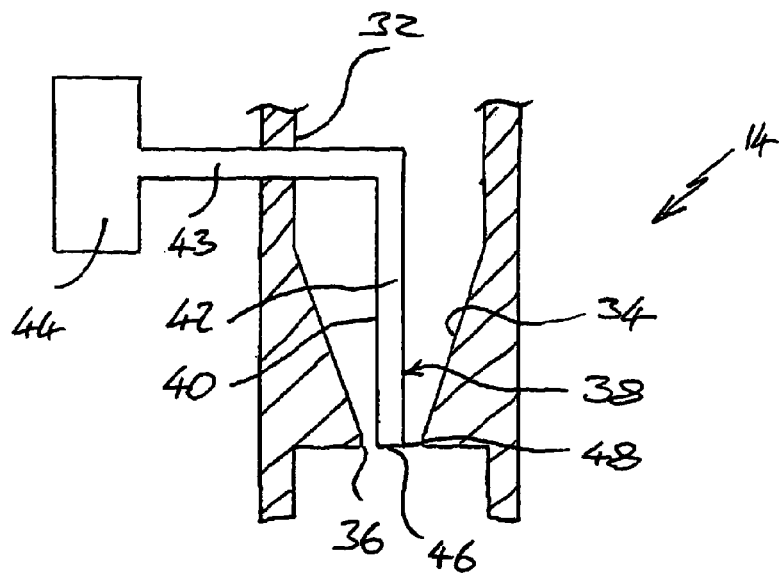
FIG. 2 is a schematic cross section through the die shown in FIG. 1.

FIG. 2 shows a schematic cross section through the die 14 of FIG. 1. The die includes an entry portion 32, a convergent portion 34 and an orifice 36 which has a predetermined outer shape. The melt enters the entry portion 32 of the die 14, is gradually shaped by the convergent portion 34 until the melt exits the orifice 36.

The die 14 further includes needles 38 (only one of which is shown in this figure) positioned therein. The needle 38 a body portion 40 having a conduit 42 therein which is fluidly connected to a fluid source 44 by means of a second conduit 43 passing through a wall of the die 14 around which the melt must flow to pass to the orifice 36. The needle 38 further includes an outlet 46 at an end 48 of the needle 38. The needle 38 is arranged such that the outlet 46 is located within the orifice 36.

Figure 3:
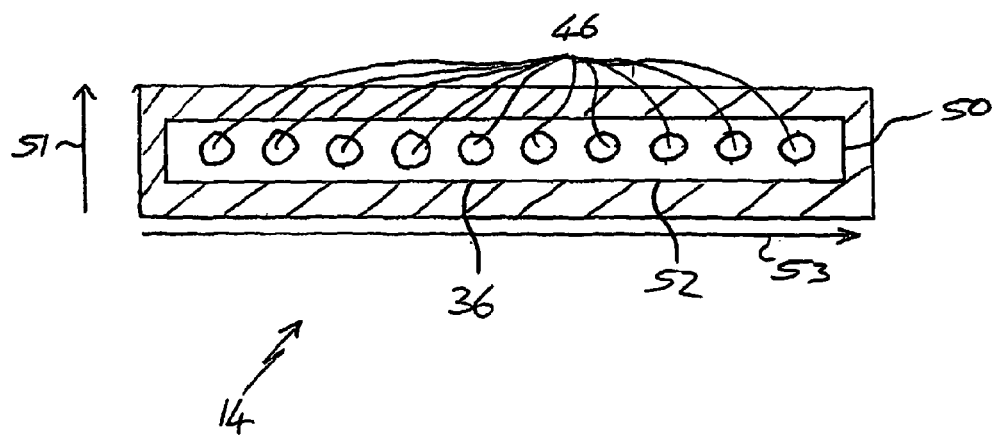
FIG. 3 is a schematic view from below of the die shown in FIG. 1.

FIG. 3 shows a schematic view of the die 14 from below. This drawing shows that the orifice 36 has a rectangular outer shape. The orifice has a short side 50 substantially parallel with a short axis 51 and a long side 52 substantially parallel with a long axis 53.

In this example, the die includes ten needles 38 with the outlets 46 distributed substantially evenly along the long axis 53 within the orifice and substantially centrally in orifice along the short axis 51. In this example, the die orifice has a short side dimension of 1.5 mm, a long side dimension of 18 mm and the needles have a 0.5 mm outer diameter and a 0.3 mm inner bore.

In an example process, a polymer melt is produced in a screw extruder 4 and its resultant flow rate stabilised by means of a gear pump 12. This melt is then fed into a die 14 in the orifice of which is arranged a plurality of outlets from needles 38 in a predetermined pattern. A conduit 42 through each needle 38 is fed from a horizontally orientated feed conduit 43, the entrance of which is open to atmosphere outside of the die which is the fluid source 44. The resulting extrudate is then passed over a series of rollers 30 into a haul-off device (not shown). The speed of the haul-off device can be altered so that extrudate products 2 with differing draw ratios can be produced.

The die 14 is designed such that the incoming flow from the extruder, which is contained in a circular pipe, is altered such that it may pass through the orifice 36 of the die 14. The die 14 must effect this geometry change, and this is currently achieved by using a convergent die 14.

The die 14 is also designed so that the flow over the array of needles 38 is substantially even. An even melt flow around the needles 38 facilitates creation of well formed extrudate 28. If, however, there is an uneven flow, the melt will preferentially channel along a path of least resistance. This results in a distorted extrudate 28.

In WO 2005/056272, the process is operated at about 165° C. using linear low density polyethylene (LLDPE). The motor 6 is controlled using a pressure feedback loop that is set to 300 PSI and this, in turn, causes a pressure of around a few bar in the die 14. Air is entrained as a result of the polymer flow over the array of needles 38 and the feed to this needle 38 array is left open to the atmosphere. The velocity of the polymer melt at the die orifice 36 is of the order of one centimeter per second, the velocity of the haul off device can be set anywhere between zero and 9 meters per minute.

The parameter that was found to have substantial influence on the final product was the distance L 29, shown in FIG. 1 and defined to be the distance between the die exit and the first roller 30. In fact, in this case the first roller is a stationary polished stainless steel rod submerged in a water bath.

The effect of variation of L is explained in further detail in WO 2005/056272.

FIGS. 4-7 illustrates some general considerations relating to immunoassays carried out in standard microtitre plate wells compared with capillary bores. It is possible to show that the geometry of a capillary allows substantial savings in reagents and time to carry out an immunoassay.

The working liquid volume and surface area of plastic in contact with the working liquid were calculated. (a) A microwell of the indicated dimensions filled with a range of working volumes from 50 µl to 300 µl and (b) a capillary of internal diameter from 50 µm to 400 µm with a length from 5 mm to 50 mm. The surface area and volume for these were plotted in (c), and the maximum diffusion distance was plotted in (d).

Figure 4:
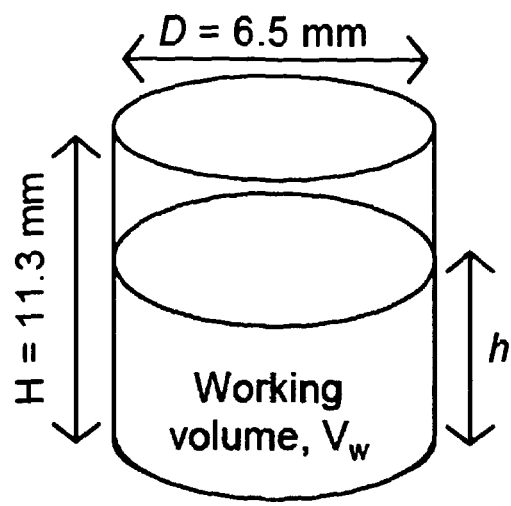
FIGS. 4-7 illustrate the effect of volume and surface area for an immunoassay in a microtitre well (FIG. 4) and a capillary bore (FIG. 5).
Figure 5:
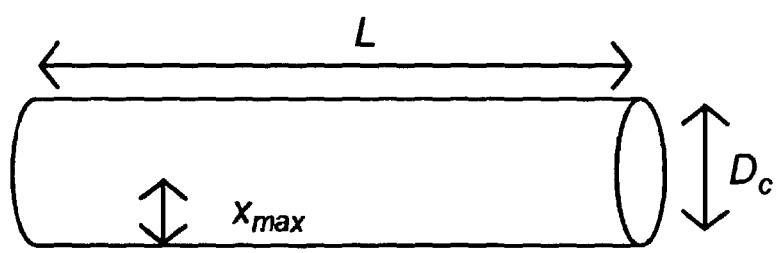

In FIGS. 4-7, consideration is given to the relevance of volume and surface area for an immunoassay. FIG. 4 illustrates schematically an IA carried out in a microtitre well plate. The height of the well is 11.3 mm and the diameter is 6.5 mm. The depth of the working volume $V_W$ is variable h and $V_W$ is taken to vary between 50 µl and 300 µl. In contrast, FIG. 5 shows schematically the bore of a capillary. The length is L and the diameter is $D_C$. $x_{max}$ is the maximum distance that a species must diffuse to reach the internal surface of the capillary bore. For the capillary, the internal diameter is taken to be from 50 µm to 400 µm with a length from 5 mm to 50 mm.

Figure 6:
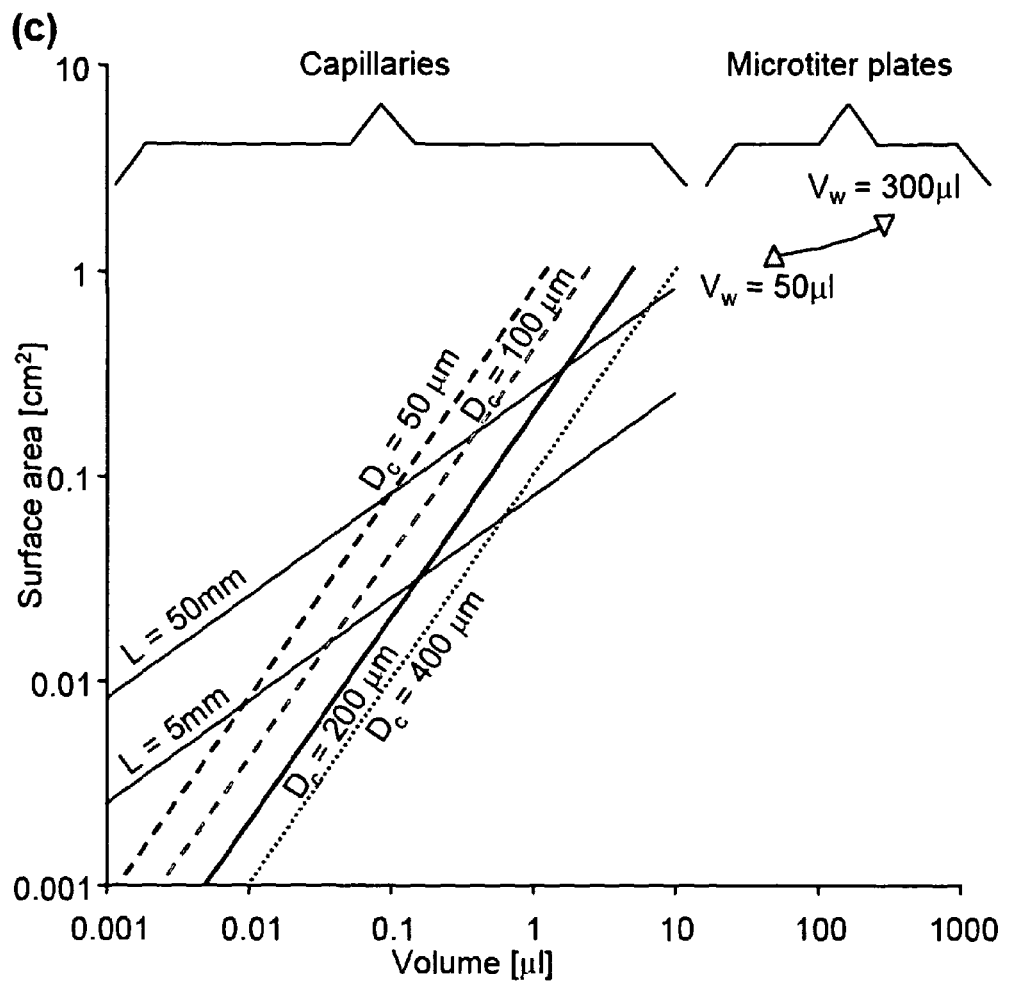
Figure 7:
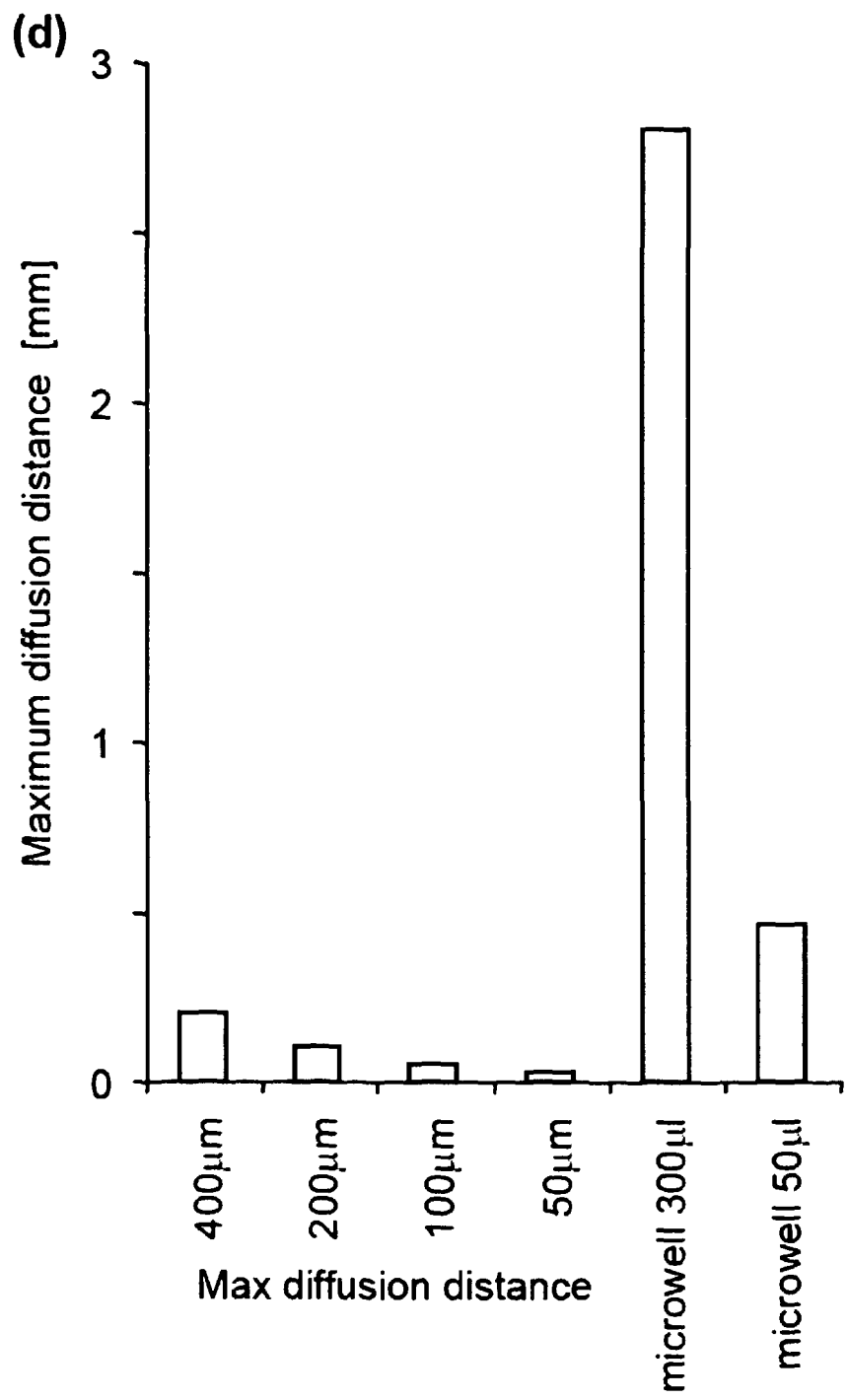

FIGS. 6 and 7 show the direct impact in diffusion distance provided by practical lengths of capillaries (in the range 5-50 mm), compared to standard microtitre plate wells. Several important conclusions can be drawn from these figures:

- In a 200 µm i.d. (inner diameter) microcapillary, the maximum diffusion distance is five times smaller than for a 50 µl microliter in a microwell plate, (note the standard sample volume for an ELISA in microwell plates is 100 µl). Following Einstein's law for diffusion distance, $x=\sqrt{(2Dt)}$, where x is the diffusion distance and D the molecular diffusion coefficient of the protein, a 25- to 100-fold reduction in incubation times can be obtained for a diffusion-controlled immobilisation process by using a microcapillary. For sensitive ELISA, where all available analyte must be given long enough to diffuse to a surface with an immobilised capture antibody, the range of incubation times can be reduced from 2-16 hours to 1-40 minutes.
- The volume within capillaries is much lower for a given surface area. This means that less reagent and sample are required to carry out the same IA.
- In a microcapillary the surface to volume ratio is far higher than for a typical microtitre plate well, therefore the sensitivity of the IA is not reduced.

Figure 8:
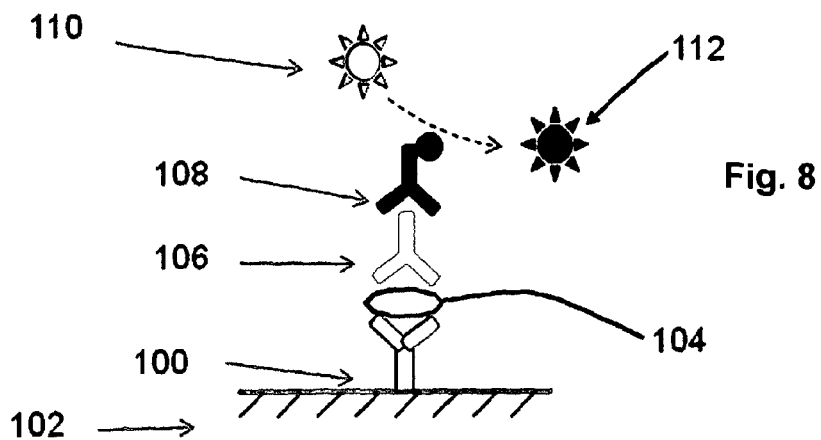
FIG. 8 shows schematically the process of an ELISA.

FIG. 8 shows schematically the process of an ELISA. An antibody 100 is captured (immobilised) at a surface 102. Analyte 104 present in a sample binds to the antibody 100. A detecting antibody 106 binds to the analyte 100 and an enzyme-linked secondary antibody 108 binds to the detecting antibody 106. Substrate 110 interacts with the enzyme-linked secondary antibody 108 to provide a detectable signal 112

Figure 9:
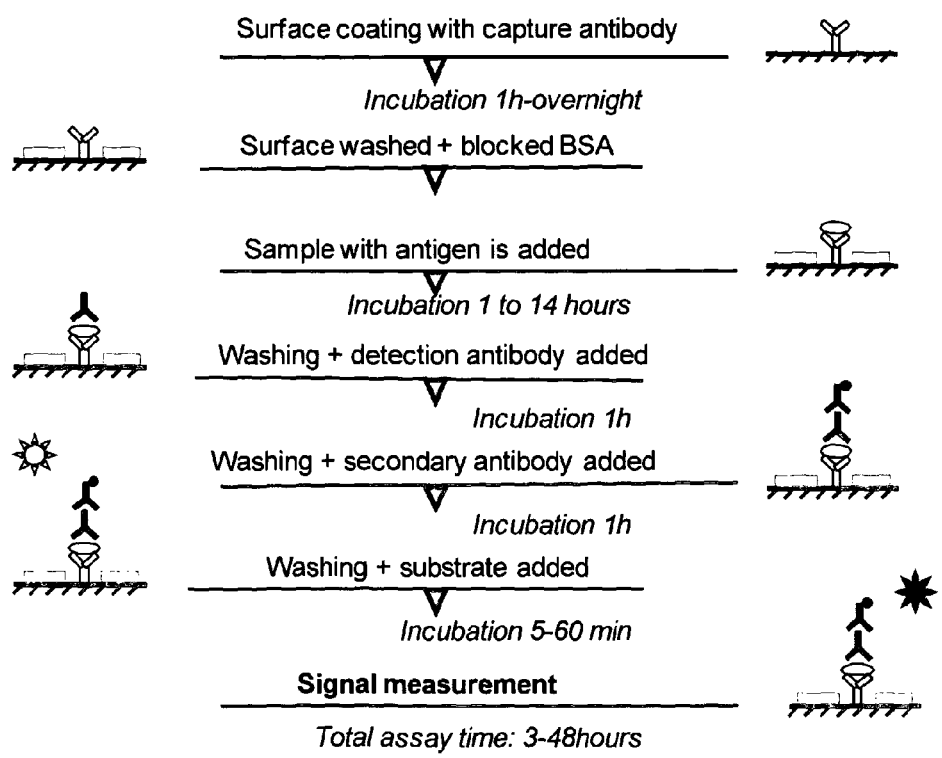
FIG. 9 illustrates the different steps of the ELISA in more detail.

FIG. 9 illustrates the different steps of an ELISA in more detail. Typically, the total time taken for an ELISA is in the range 3-48 hours.

Figure 10:
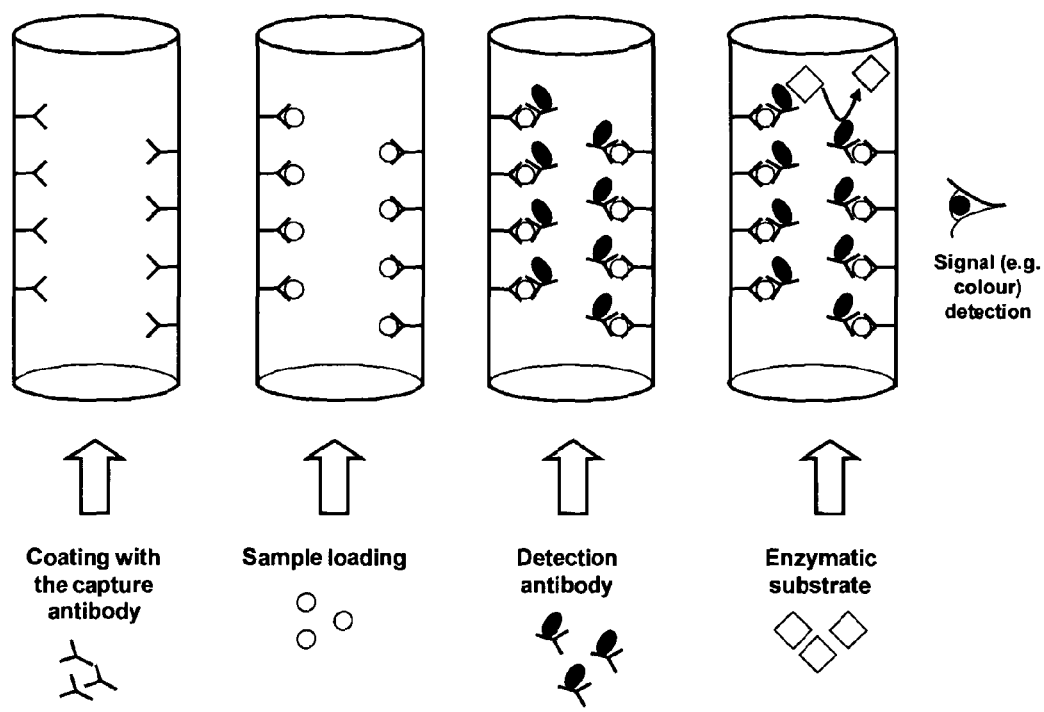
FIG. 10 illustrates the steps of an immunoassay carried out in a capillary bore.

FIG. 10 illustrates the steps of an immunoassay carried out in a capillary bore.

Figure 11:
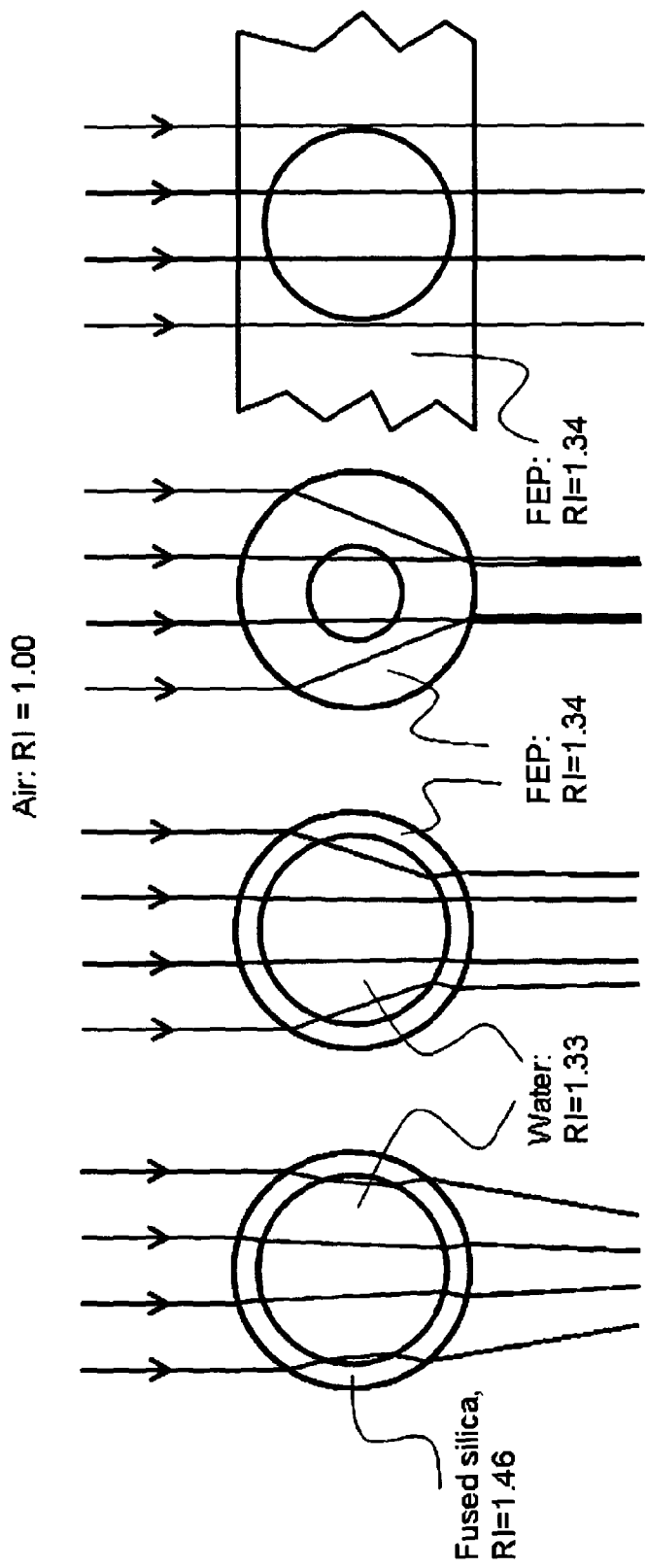
FIGS. 11A-D illustrate the effect of refractive index of the body of the capillary immunoassay device on optical distortions during optical interrogation.

The inventors have realised that one significant drawback to using known capillary-based immunoassays relates to optical interrogation of the capillary bore. This is illustrated in FIG. 11A-D. FIGS. 11A and 11B show a typical capillary device formed from fused silica. An aqueous sample fluid (water in this case) is located in the capillary bore. As shown in FIG. 11A, refraction of light transiting the device occurs at the interface between the air and the body of the device and also at the interface between the body of the device and the sample fluid in the bore. This is due to changes in refractive index at those interfaces. The refractive index of air is 1.0, the refractive index of water is 1.33 and the refractive index of fused silica is 1.46.

However, as shown in FIGS. 11C and 11D, the effect of refraction at the interface between the body of the device and the bore can be reduced or even avoided by forming the body of the device using a material having a refractive index close to or the same as that of the sample fluid (water in this case). Suitable materials include Fluorinated Ethylene Polypropylene (FEP) with a refractive index of 1.34; Tetrafluoroethylene hexafluoropropylene vinylidene fluoride (THV) with a refractive index of 1.35; Perfluoroalkoxy (PFA) with a refractive index of 1.34; Ethylene Tetrafluoroethylene (ETFE) with a refractive index of 1.40; and Poly(chlorotrifluoroethylene) (PCTFE) with a refractive index of 1.39.

Fluorinated Ethylene Polypropylene (FEP) is considered to be particular suitable for immunoassay applications because it is hydrophobic. It is therefore effective for adsorbing proteins at the walls of the capillaries. However, it is not essential for the material to be hydrophobic. As the skilled person understands, there are many different types of surface modifications that can be made in order to immobilize antibodies.

Furthermore, the present inventors have realised that an immunoassay can be carried out in one or more capillary bores of an extruded microcapillary film (MCF). The immunoassay can be multiplexed, using the different available capillary bores of the MCF.

MCF can be used to form the basis of a new platform (herein named as Extruded Array ImmunoAssay, EAIA) for IA, providing a simple and cost effective method for multiplexed IAs using a single sample connection. The key aspects of the preferred embodiments of this invention involve:

1. Coating each individual microcapillary with a specific antigen or capture antibody. This can be done by passing appropriate solutions down respective channels of an MCF that may be several meters in length. In this way, where the MCF has 20 capillary bores, 20 different coatings are applied to a 20-channel MCF.

2. The MCF can then be cut into lengths of, e.g., 1 cm. Each length can be then fitted to a simple suction tube. This represents a very effective manufacturing route for each batch tester.

3. Operation is effected by drawing the test fluid into the channels of the MCF and then following the colour contrast for each individual MCF channel.

4. Detection can be visual or automated in order to make the measurement quantitative.

Extruded FEP MCF is available from Lamina Dielectrics, Ltd., Daux Road, Billingshurst, West Sussex RH14 9SJ, United Kingdom.

Figure 12:
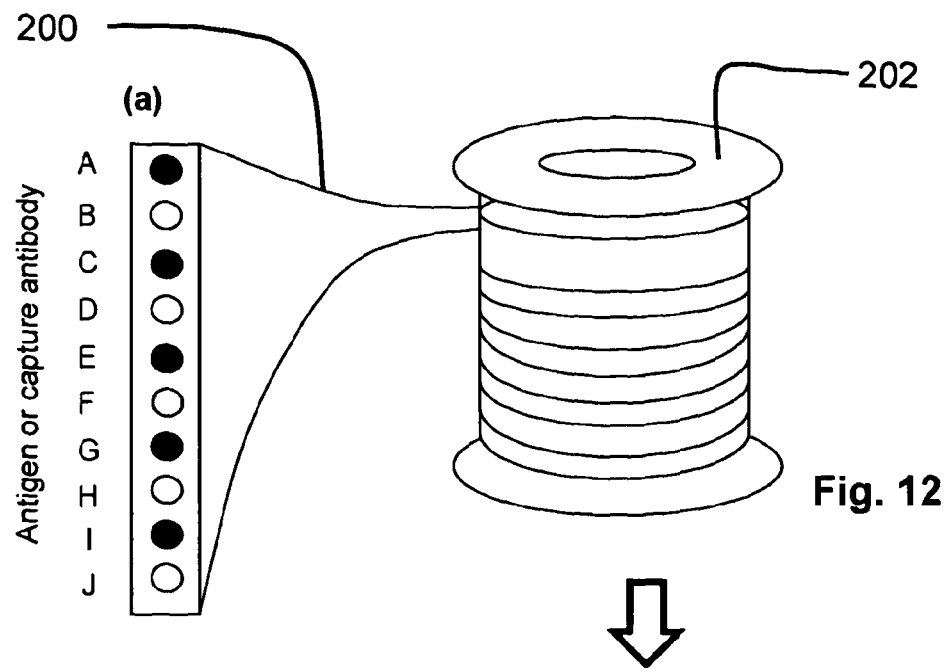
FIG. 12-14 illustrate a method of manufacturing an immunoassay device according to an embodiment of the present invention. Another manufacturing method comprising an additional step of separating the capillaries of the immunoassay device at one end of the device is shown in FIGS. 39-40.
Figure 13A:
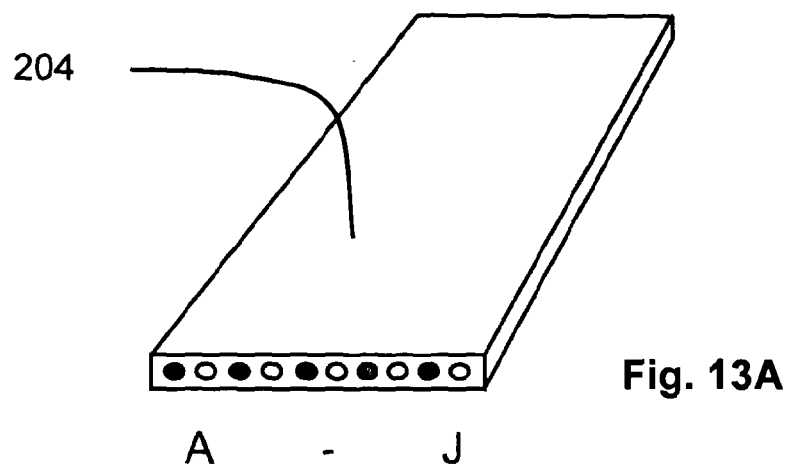
Figure 14:
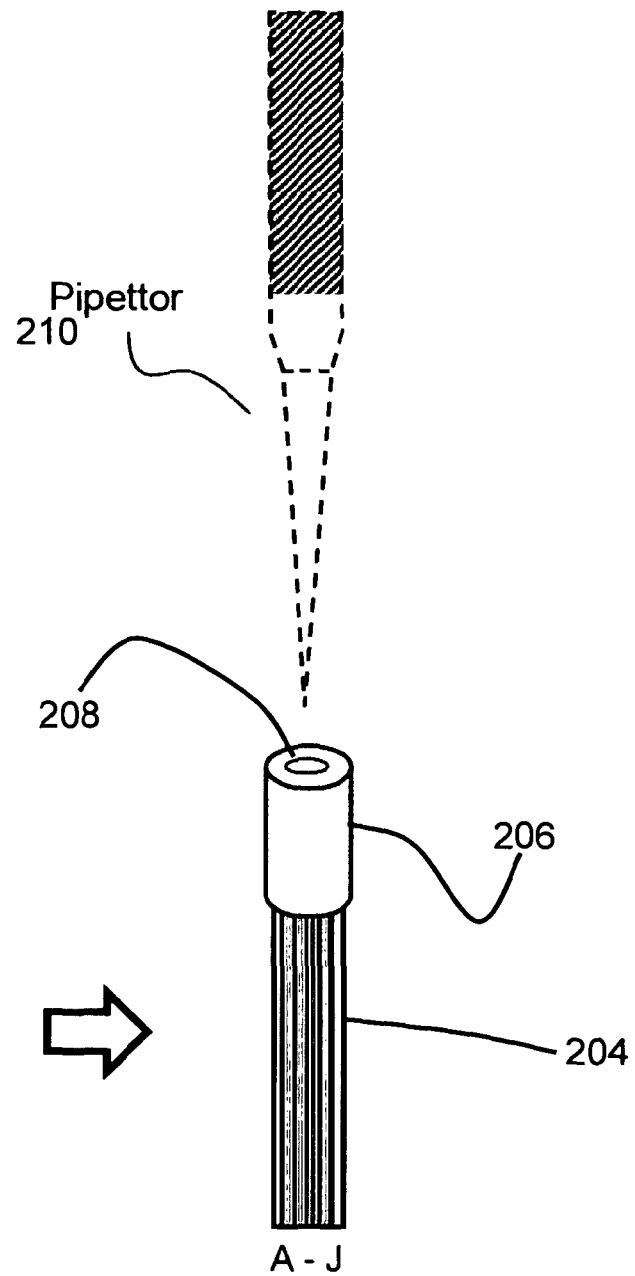

FIGS. 12-14 illustrate a method of manufacturing an immunoassay device according to an embodiment of the present invention.

In FIG. 12, a length of microcapillary film 200 is provided on a reel 202. The film is manufactured from FEP, as discussed above. The total length of the microcapillary film can be, for example, at least 1 m. Longer lengths, e.g. up to 10 m, 20 m, or longer still can be manufactured via the extrusion process discussed above.

Subsequently, it is possible to load each microcapillary with an antigen or capture antibody. This may be done, for example, using a syringe and needle. This is the preferred route where each microcapillary is to be loaded with a different antigen or capture antibody, or with a different concentration of such species. As explained in more detail below, the present inventors have found that, surprisingly, the uniformity of the adsorption of the antigen or capture antibody along the length of the microcapillaries is very high. Conveniently, the loading step can be carried out whilst the MCF remains on a reel. Where it is wanted to load each microcapillary identically, this can be carried out by dipping one end of the MCF into a single loading solution, this loading solution being aspirated into each microcapillary bore using a single aspirator (not shown) at the opposite end of the MCF. Where it is wanted to load one or more microcapillaries differently, the microcapillaries can be separated at one end of the MCF, either into individual microcapillaries or into set of microcapillaries. Separation may be achieved by cutting the film between the capillaries. Separating the microcapillaries in this way, facilitates contacting each microcapillary, or set of microcapillaries, with a different loading solution. This is useful where each microcapillary or set of microcapillaries is to be loaded differently. The loading solution can be aspirated into each microcapillary bore or set of microcapilary bores, using a single aspirator. Alternatively, a separate aspirator can be used for each capillary or set of capillaries. The aspirator may, for example, be a pipette or a syringe.

As shown in FIG. 12, each capillary is given a letter designation A-J. In this case, different microcapillary bores are loaded with different antigens or capture antibodies.

Subsequently, the loaded microcapillary is cut to a desired length (e.g. 5-50 mm), as shown in FIG. 13, to form an immunoassay device 204. As will be understood, the long reel of MCF can be used to form very many immunoassay devices. Therefore only a single loading step is required, even though very many immunoassay devices are produced.

Next, as shown in FIG. 14, the immunoassay device 204 can be used to carry out an immunoassay. One end of the device is connected to an adaptor 206. In this example, adaptor 206 has a simple structure, sealing to the device at one end and providing an orifice 208 at its opposite end. Orifice 208 allows sealing with an aspirator, shown in this case as a conventional laboratory pipettor 210. When the free end of the device 204 is dipped into a sample fluid, operation of the pipettor draws the fluid along the bores. Subsequent steps (e.g. those indicated in FIGS. 9 and 10) can be carried out in a similar manner.

Figure 38:
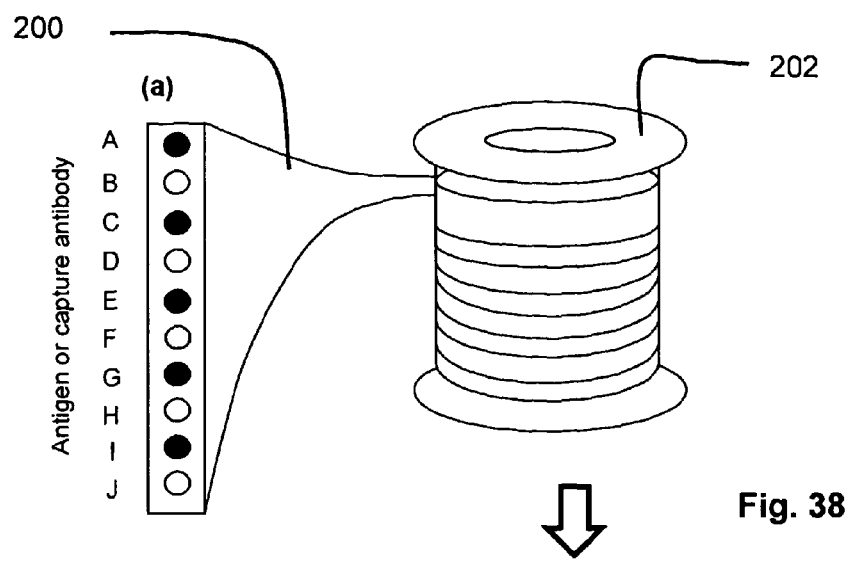
FIG. 38-40 illustrate a method of manufacturing an immunoassay device according to an embodiment of the present invention. In this case, the capillaries of the immunoassay device are separated at one end of the device to facilitate uptake of different samples into each of the capillaries.
Figure 39:
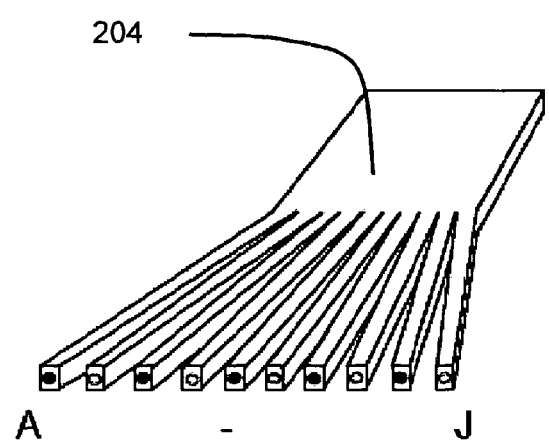
Figure 40:
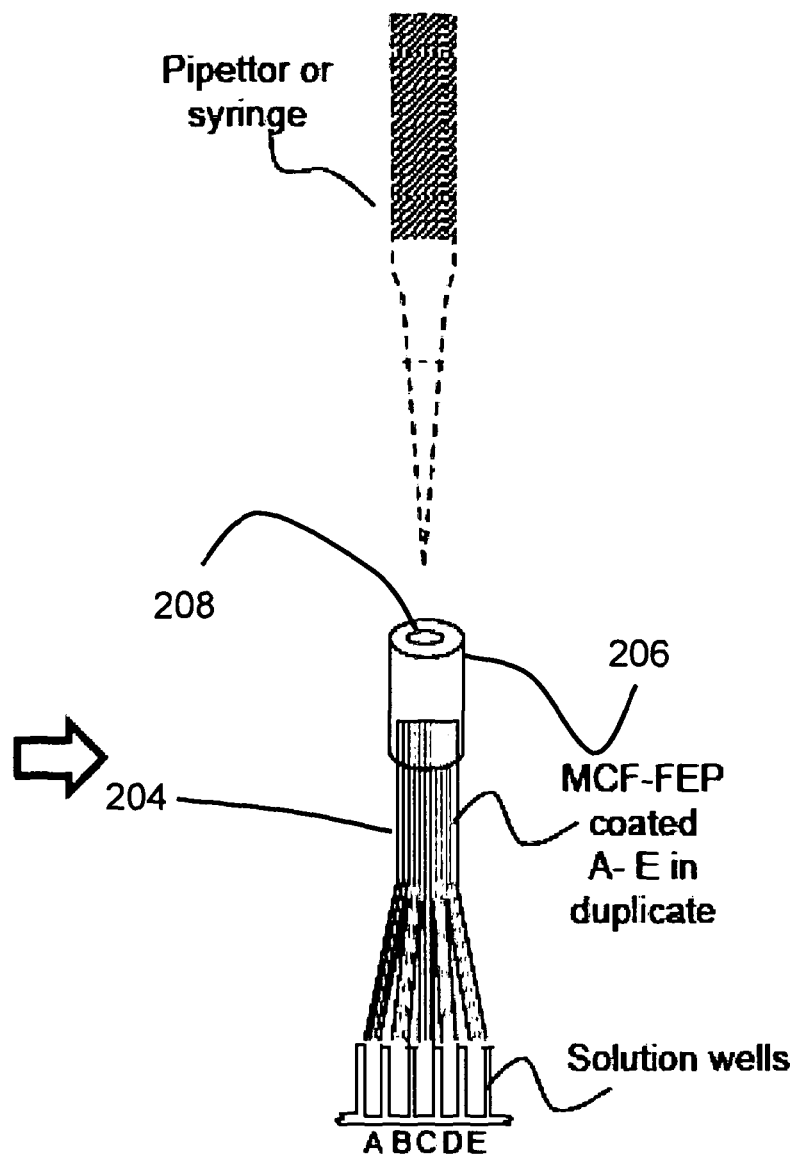

Another method of manufacturing an immunoassay device according to an embodiment of the present invention is shown in FIGS. 38-40. FIG. 38 is identical to FIG. 12 already described above. As before, the loaded microcapillary film is cut to a desired length (e.g. 5-50 mm), to form an immunoassay device 204 (FIG. 39). In FIG. 39, the microcapillaries are additionally separated at one end. Separation may be achieved by cutting the film between the capillaries. This facilitate, for example, loading of the microcapillaries with different samples. Sample loading may, for example, be done by contacting each microcapillary, or set of microcapillaries with a different sample tray (FIG. 40). This is useful where each microcapillary or set of microcapillaries is to be used to analyze a different sample, or the same sample but at different levels of dilution. The sample fluid can be aspirated into each microcapillary bore using a single aspirator. Alternatively, a separate aspirator can be used for each capillary or set of capillaries. The aspirator may, for example, be a pipette or a syringe. In FIG. 40, the immunoassay device 204 is connected to an adaptor 206. In this example, the adaptor 206 seals the device at one end and provides an orifice 208 at its opposite end. Orifice 208 allows sealing with an aspirator, shown in this case as a conventional laboratory pipettor 210. When the free ends of the device 204 are dipped into sample fluids provided in different trays, operation of the pipettor draws the fluid along the bores. Subsequent steps are carried out as described above.

Figure 15:
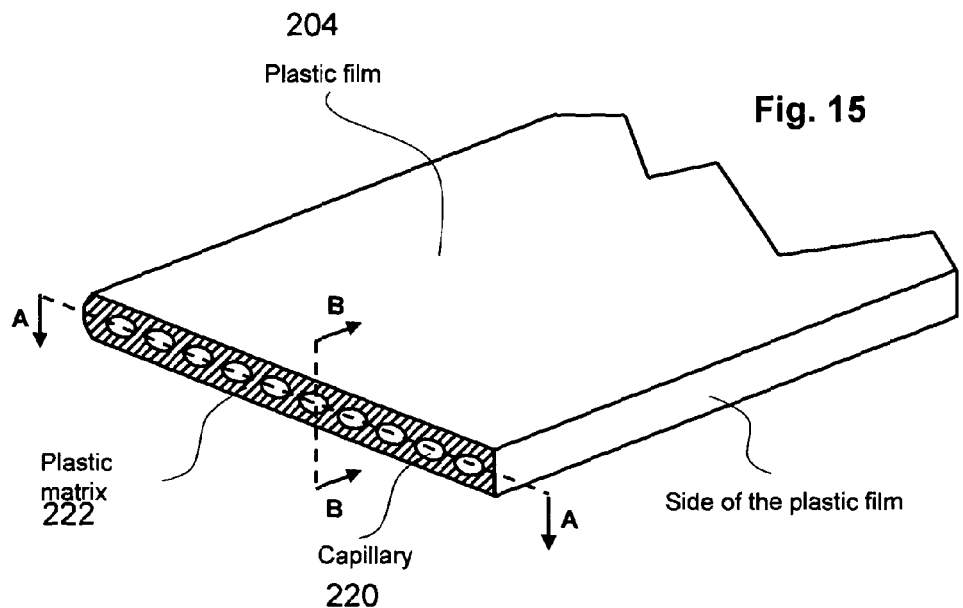
FIGS. 15-17 show more detailed views of parts of the loaded microcapillary film immunoassay device according to a preferred embodiment of the present invention.
Figure 16:
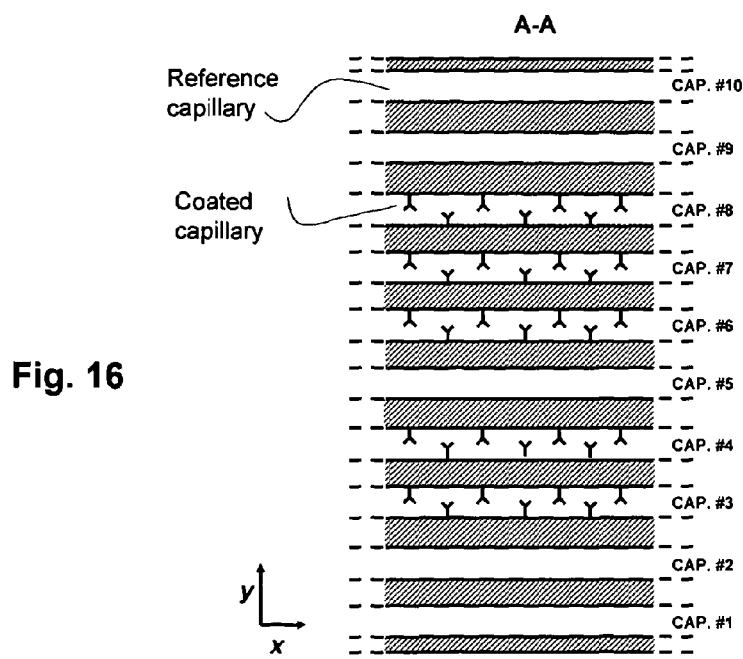
Figure 17:
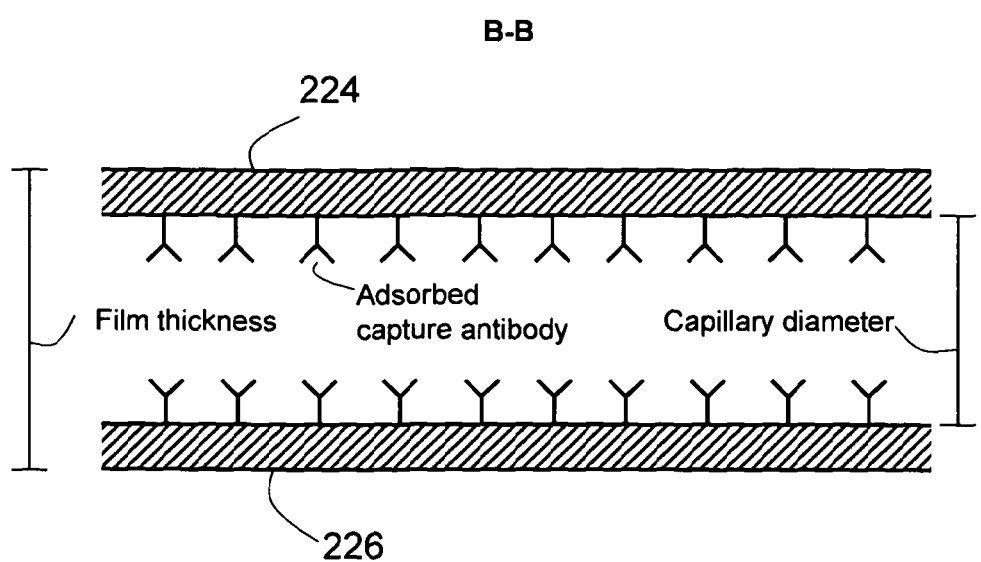

FIG. 15 shows a more detailed view of part of the loaded microcapillary film immunoassay device 204. FIG. 16 shows a view along section A-A and FIG. 17 shows a view along section B-B in FIG. 15. As can be seen in these drawings, the device 204 has a flat lower surface and a flat upper surface. These surfaces correspond to the measurement first surface and the measurement second surface, since during optical interrogation, light is transmitted to and from the capillary bores via these surfaces.

As shown in FIG. 15, the individual microcapillary bores 220 have a generally oval shape. The plastic matrix 222 of the device is formed from FEP and is transparent to visible light. The width of the device is in the range 5-20 mm. The thickness of the device (including the microcapillary bores 220) is in the range 0.2-2 mm.

FIG. 16 illustrates that each capillary bore can have a different loading of antigen or capture antibody. As shown in FIG. 16, it is preferred to form a reference capillary having no loading.

It is preferred that the top 224 and bottom 226 surfaces of the MCF (see FIG. 17) are substantially flat. The reason for this is that a flat surface, normal to the direction of transmitted light during interrogation of the immunoassay device, will typically provide minimal (or even zero) disadvantageous optical effects.

Figure 18:
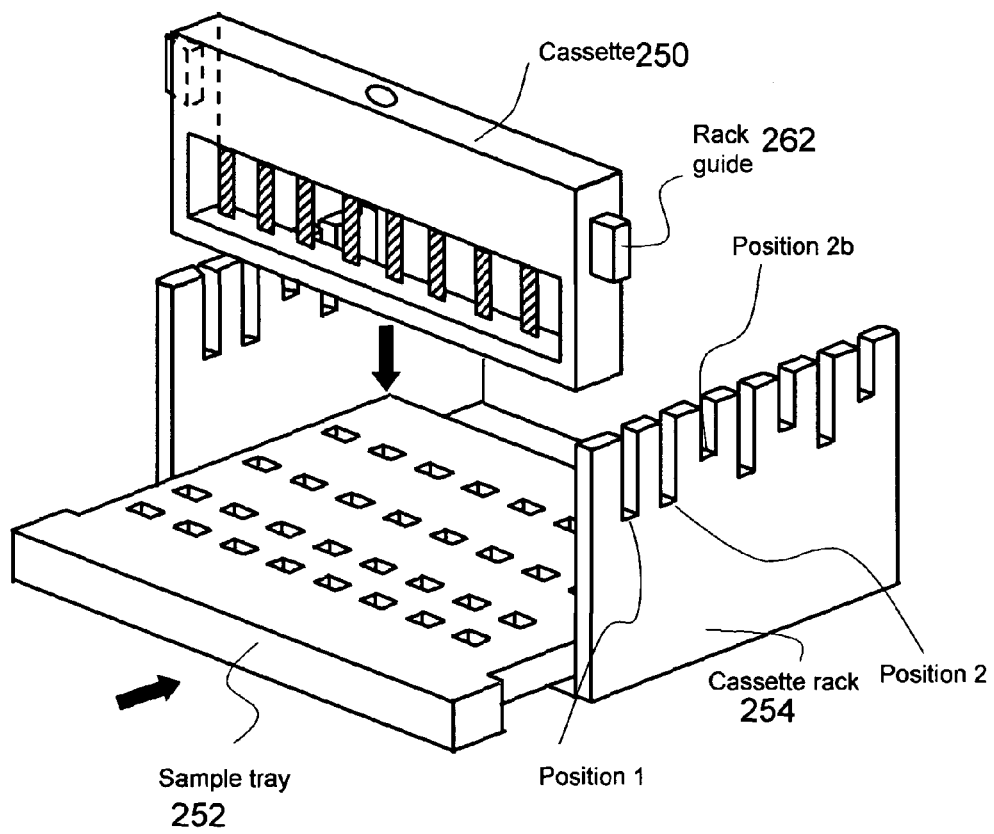
FIG. 18 shows the assembly of an immunoassay system for multiple samples according to a preferred embodiment of the present invention.

FIG. 18 shows the assembly of an immunoassay system according to a preferred embodiment of the present invention. The system has three main components: cassette 250, sample tray 252 and cassette rack 254. The cassette 250 and the sample tray 252 are shown in more detail in FIGS. 19 and 20.

Figure 19:
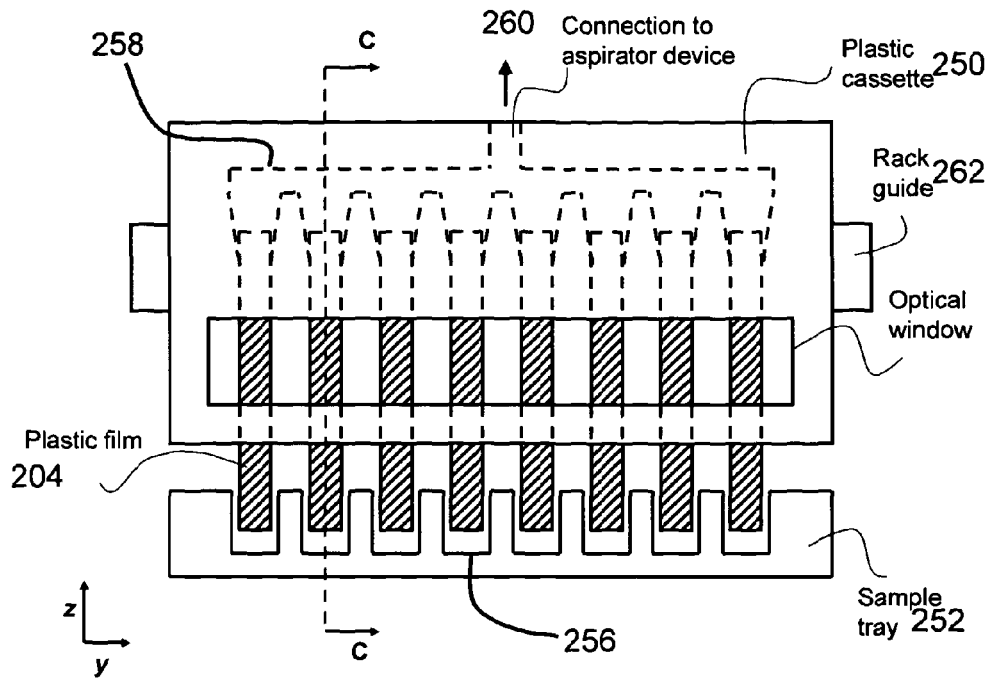
FIG. 19 shows a plan view of the cassette of the immunoassay system of FIG. 18.
Figure 20:
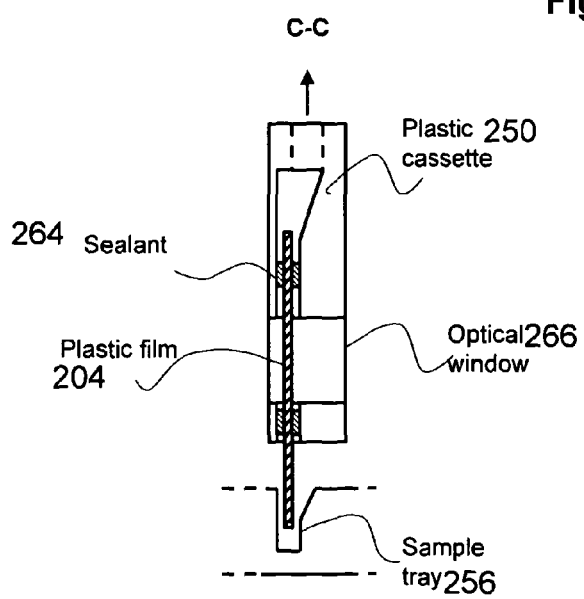
FIG. 20 shows a side view of the cassette of the immunoassay system of FIG. 18.

As shown in FIG. 19, several (eight, in this example) MCF immunoassay devices 204 are held in cassette 250. The free ends of the immunoassay devices extend from the bottom of the cassette to dip into wells 256 in sample tray. The upper ends of the immunoassay devices are held in the cassette such that the capillary bores are in sealing communication with a fluid flow manifold 258, the manifold 258 leading to a connection orifice 260 at the top of the cassette, for connection to an aspirator device. As shown in FIG. 20, sealing between the immunoassay devices and the manifold is provided by sealant 264.

In order to carry out an EAIA, for example, the end-user would process each cassette sequentially along the different rows of slots of the cassette rack, the rows corresponding to a series of washing (position 1), sample loading (position 2) and incubation steps (position 2b) (FIG. 18). Note that for the incubation step, the ends of the MCF immunoassay devices are not dipped in any sample wells. Samples and antibody solutions can be pre-loaded in the disposable sample tray to avoid cross-contamination. After dipping the ends of MCF immunoassay device into a given set of wells, the fluid in the wells is drawn into the capillary bores using a fluid flow manifold. The capillary bores do not need to be emptied between the different steps of the assay, as the new fluid being drawn into the capillary bores replaces any fluid already present.

Figure 21:
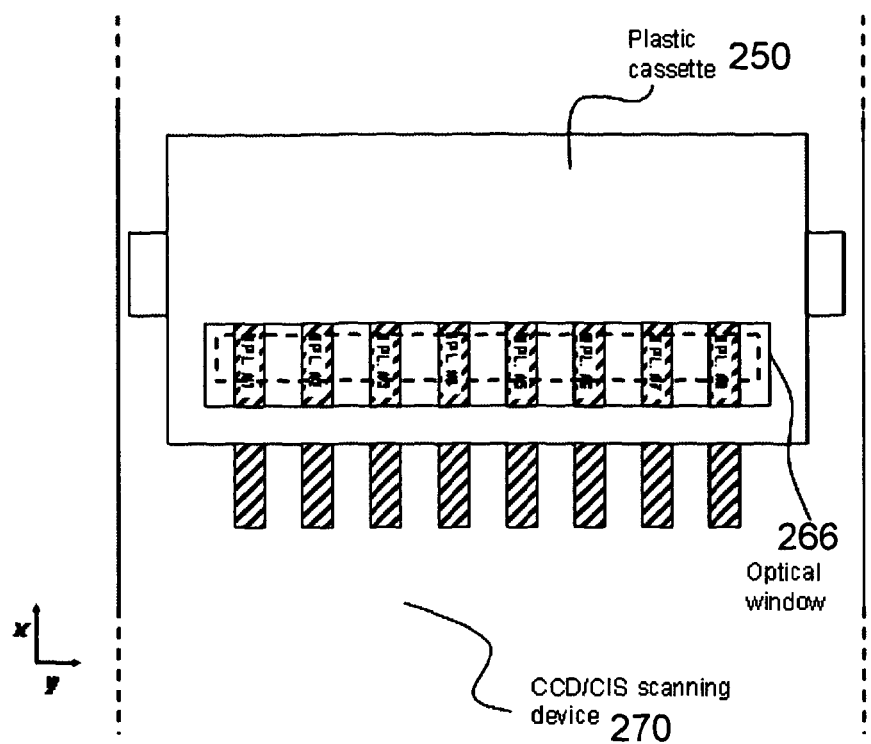
FIG. 21 shows the cassette of FIG. 18 being scanned on a flatbed scanner.

The cassette 250 includes rack guide lugs 262 to enable the cassette to be located at each desired position in the cassette rack. The cassette also has a window 266 to allow the user to observe the progress of any available visual change in the immunoassay devices. In addition, the window provides optical access to the immunoassay devices during optical interrogation, e.g. using a digital camera or (more preferably) using a flatbed scanner. This is shown in FIG. 21, the cassette 250 being scanned on a flatbed scanner 270.

Using the scanner 270, the light transmitted through each MCF immunoassay device can be determined based on pixel analysis of the scanned image. The skilled person will understand how this can be done using a standard image processing software.

Figure 22:
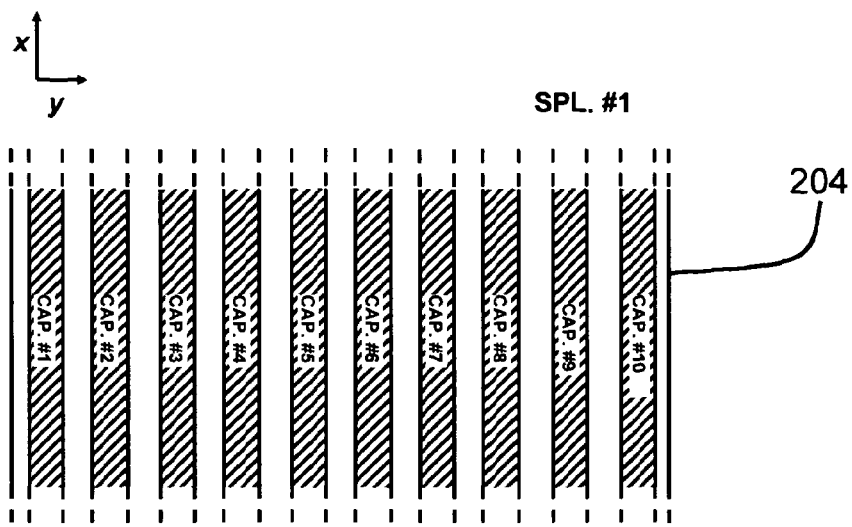
FIG. 22 shows an enlarged view of a portion of a MCF immunoassay device, as seen through a window of the cassette.

FIG. 22 shows an enlarged view of a portion of a MCF immunoassay device 204, as seen through the window 266 of the cassette. In the scanning process, each of the capillary bores is imaged under substantially the same conditions. Furthermore, the flat upper and lower surfaces of the immunoassay device and the small (or zero) difference in refractive index between the material of the immunoassay device and the fluid contained in the bore ensures that a useful measurement can be taken of pixel intensity across all (or at least most of) the width of each capillary bore.

Figure 23A:
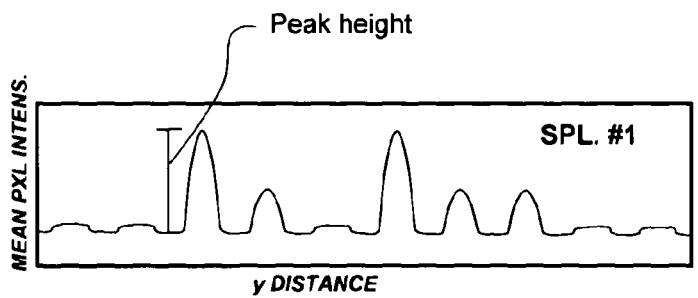
FIGS. 23A and 23B show schematic plots of pixel intensity across respective different immunoassay devices in the same cassette.
Figure 23B:
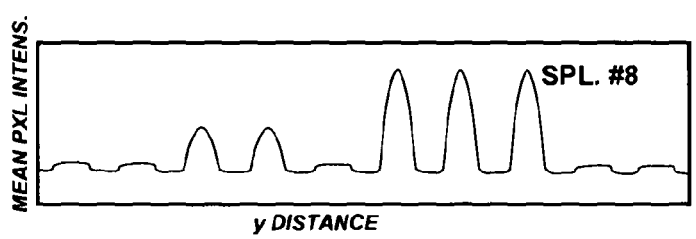

FIGS. 23A and 23B show schematic plots of pixel intensity across respective different immunoassay devices in the same cassette. Thus, quantitative measurements of the immunoassay are made possible via this simple technique.

Figure 24A:
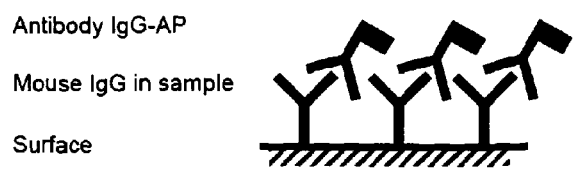
FIGS. 24A-C show the evaluation of antibody adsorption and signal detection in an MCF-FEP.
Figure 24B:
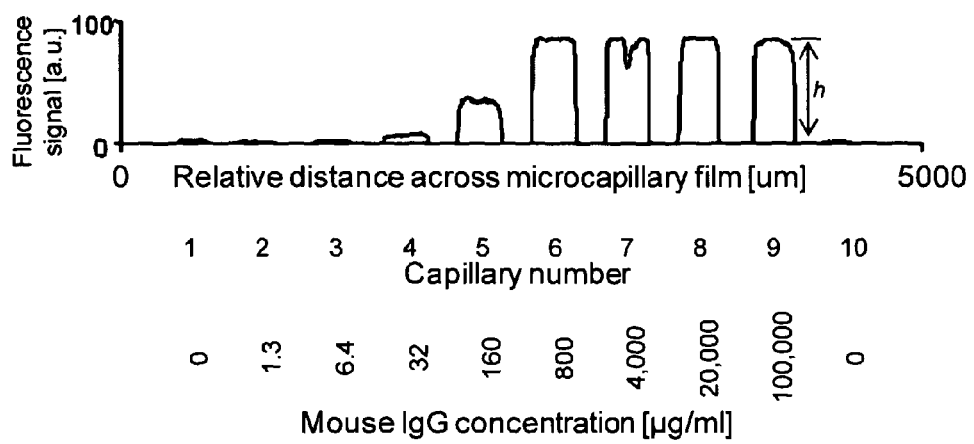
Figure 24C:
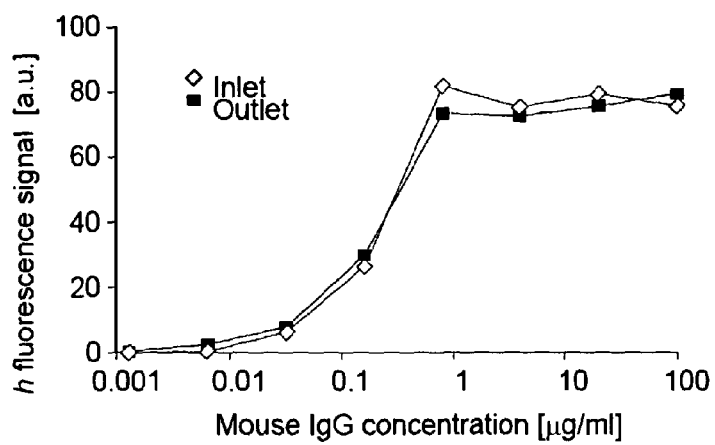

FIGS. 24A-C show the evaluation of protein immobilisation and signal detection in an MCF-FEP. The capillaries within a 5 m reel of MCF-FEP were individually coated with the indicated concentrations of IgG or buffer control, followed by blocking and washing. Then, 50 mm long pieces were cut, attached to an adaptor and incubated with anti-mouse-HRP (horseradish peroxidase), followed by washing and uptake of the substrate FDP. After 60 minutes, the fluorescent converted FDP was imaged using confocal laser scanning microscopy.

FIG. 24A shows a schematic representation of the enzyme-linked immunosorbent assay in the MCF-FEP.

FIG. 24B shows a plot of mean fluorescent intensity across the capillary array. The mouse IgG concentration present in each capillary is indicated below the plot.

FIG. 24C shows a plot of height, h, of grey fluorescent intensity measured at the inlet and outlet of a 5 meter reel of MCF, indicating no depletion of the IgG after running through the capillary. This result illustrates the surprising uniformity of loading possible in the immunoassay device, even when loading is carried out in a single step on a reel of the extruded microcapillary film.

FIGS. 24A-C show that antigen proteins or antibodies can be effectively immobilised in the internal surface of the extruded array of microcapillaries. These figures summarise the effectiveness of antibody immobilisation on internal surface of a 10 capillary FEP-MCF. Several points are demonstrated for using a fluorescent substrate and confocal microscopy:

The amount of protein bound at the inlet and outlet of a 5 m length is the same across a range of input protein concentrations; this demonstrates the possibility of coating in one long strip, followed by cutting multiple pieces for different samples.

Different concentrations of coating protein in individual capillaries clearly lead to different signal response, therefore validating the platform for quantitative IAs.

Figures 25A, 25B:
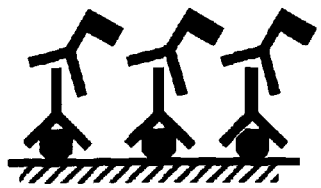
FIGS. 25A and 25B demonstrate multi-analyte detection using an extruded array of capillaries.

FIGS. 25A and 25B show that multi-analyte detection is possible using the extruded array of capillaries.

The capillaries in a reel of a MCF-FEP were individually coated with 4 different antigens (A-D), namely buffer control (A), positive control mouse IgG (B) or the antigens FLAG peptide (C) or Hepatitis B Core antigen (D). The order of these coating is indicated by the relevant letter A-D next to the respective capillary bore shown at the left hand side of FIG. 25A. After blocking and washing, 50 mm long pieces were cut, attached to an adapter and incubated with 3 different test samples (1-3) containing the antibodies anti-HB/CAg or anti-FLAG or buffer control. After washing, the pieces were incubated anti-mouse IgG-HRP followed by extensive washing and addition of the substrate FDP. After 5 min the fluorescent converted substrate was imaged by confocal laser scanning microscopy. The presence or absence of strong fluorescent signal was scored + for positive, − for negative, and +/− for one capillary with intermediate signal; these scores are indicated alongside the key showing which antigens were coated in the capillary.

Thus, the ability to detect more than one antibody using a single sample fluid feeding step is demonstrated. Three different antigens (plus a negative control) were immobilised in different capillaries in a defined pattern. When different samples contained different anti-serum were tested in separate MCF pieces, the expected pattern of positives and negatives was obtained.

The extruded capillary array can also be used to perform sandwich IAs. Many IAs rely on a "sandwich" process. For example, the cancer biomarker prostrate specific antigen (PSA) is frequently measured in biological samples such as urine or blood using two antibodies (a 'capture' antibody and a 'detection' antibody) that bind to two distinct epitopes on the PSA molecule. To detect PSA using a sandwich IA, the 'capture' antibody is immobilised onto the assay surface. The capture antibody binds to PSA protein present in a sample. PSA captured by the capture antibody is detected using a 'detection' antibody, which is labelled with biotin. The amount of bound detection antibody is then detected by incubation with an enzyme conjugated to a biotin-binding molecule such as streptavidin.

A PSA sandwich IA was conducted in MCF-FEP using reagents supplied in kit form from R&D Systems (Minneapolis, Minn., USA, cat. No DY1344). A number of optimisation experiments were performed to determine the most appropriate reagent concentrations and incubation times to perform a sandwich IA to detect PSA in MCF-FEP. These experiments demonstrated the following:

1) The optimal concentration of capture antibody for coating the inside of the capillaries in MCF-FEP was found to be 10 µg/ml, in contrast to an optimal concentration of 1 µg/ml for microtitre plate ELISAs. This was expected due to the difference in the surface area to volume ratio in MCF-FEP capillaries compared with microtitre plates.

2) The optimal concentration of detection antibody was not significantly different between MCF-FEP capillaries vs microtitre plates. This was also expected since detection antibodies are often used in significant excess and therefore reducing the concentration often has little effect on assay sensitivity.

3) The optimal concentration of ortho-phenylene-diamine (OPD) substrate was higher in MCF-FEP compared to microtitre plates, Again this was expected due to the difference in the surface area to volume ratio in MCF-FEP capillaries compared with microtitre plates.

4) For optimal sensitivity, incubation times for sample and detection antibodies were significantly reduced for IAs conducted in MCF-FEP, compared to the minimum incubation times required for microtitre plate assays.

5) The reagent and wash volumes required for assays performed in MCF-FEP were 2-4-fold lower than for the microtitre plate assay.

Having optimised this IA protocol for MCF-FEP, a comparison was made between the optimised MCF-FEP IA with a microtitre plate IA performed according to the instructions supplied by the manufacturer for the kit. To allow direct comparison of assay signal, the flatbed scanner optical detection signal was converted to an absorbance reading and normalised to absorbance units per centimeter path length using equations 1 and 2:

$$Abs = -\log\left(\frac{I}{I_o}\right) \quad (1)$$

$$Abs = \varepsilon\ell[C] \quad (2)$$

For the microtitire plate assay, the path length is 0.3 cm, while for the MCF it is 0.02 cm.

Figures 36, 37:
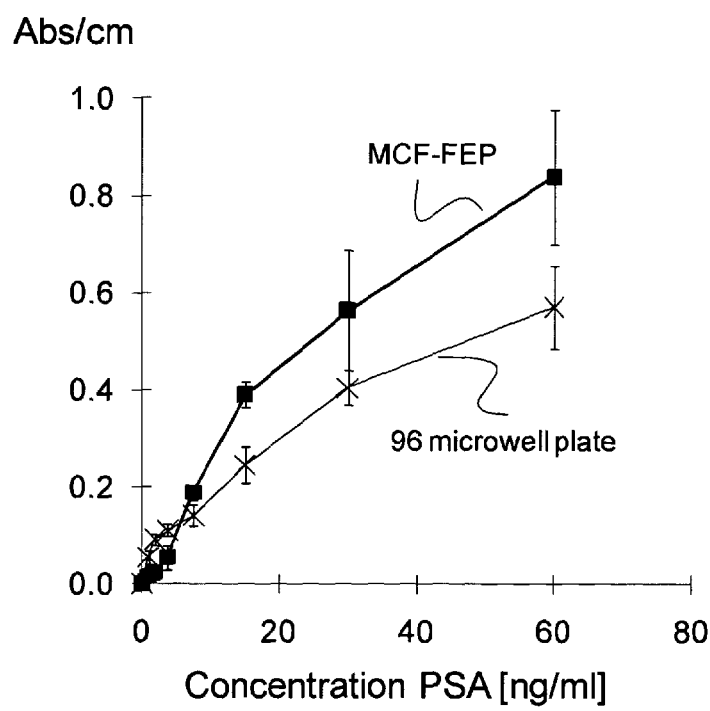
FIG. 36 shows a comparison of overall performance of a sandwich IA performed in MCF-FEP with a sandwich IA performed in a 96 microwell plate. Abs/cm denotes Absorbance per cm. The concentration of the analyte (cancer biomarker PSA) in ng/ml is indicated on the x-axis.
FIG. 37 shows a comparison of the major incubation times for a sandwich IA performed in a 96 well plate and a sandwich IA performed in MCF-FEP.

FIG. 36 shows the sensitivity of sandwich IAs performed in MC-FEP and microtitire plates is comparable.

A major advantage of sandwich IAs performed in the extruded capillary array is the time required to perform the assay. This is illustrated in FIG. 37, which shows the reduced incubation times found to be required when sandwich immunoassays are conducted in MCF-FEP in contrast to the long incubation times required for assays performed in microtitire plates. The requirement for reduced incubation times is expected to apply to all types of IAs performed in the extruded capillary array compared to IAs performed in microtitre plates. The extruded capillary arrays described herein are therefore particularly suitable for performing high throughput assays.

FIG. 26 shows a schematic view of a cross section of the format of an immunoassay device used to obtain the results shown in FIG. 27.

FIG. 27 shows images obtained from a flatbed scanner. Two short pieces of MCF-FEP were washed in PBS-Tween solution and then all capillaries filled with a solution of PBS-T or a fully converted o-Phenylenediamine dihydrochloride (OPD) substrate and then scanned at 3,200 dpi using transmitted light mode in a HP ScanJet 4050 Photo Scanner. Averaged plots of pixel intensity across the film or capillary are shown alongside a scale bar. The blue channel is also shown separately to illustrate the high absorbance of blue light by converted OPD; again, the averaged pixel intensity is shown.

Thus, capillaries can be individually cross-interrogated using cost-effective optical detectors.

Note that in obtaining the results shown in FIG. 27, two solutions were sucked through all the 10 capillaries in two pieces of MCF and then a RGB image acquired and recorded in TIF format. The image was subsequently split in the three RGB channels (i.e. Red, Green and Blue) and grey level intensity plated allowing the y-distance of the film using ImageJ. The images were scanned using a simple flatbed scanner in transmittance mode. This is a simple and cheap method for optical detection and imaging, however, the same signal detection can be expected for any other optical technique. This means of signal detection and quantification in capillaries is made practicable because of the flat surface of the MCF and the excellent optical properties of the fluoropolymer material used for the extrusion of MCF (having similar refractive index to water, therefore water-filled MCF capillaries are 'invisible'). This is further supported by subsequent FIGS. 28 and 29.

The excellent optical properties of MCF-FEP filled with aqueous liquids and the benefits of thereof for simple signal detection are demonstrated by the wide range of different imaging devices than can be used to interrogate MCF-FEP. In addition to the confocal microscope used to detect fluorescent substrate (e.g. FIGS. 24 and 25) and the HP Scanjet G4050 flatbed scanner that was used in transmittance mode utilising a cold cathode fluorescent light source and charge coupled device (CCD) image acquisition to measure ELISA substrate and blue dye within FEP MCF (e.g. FIGS. 26-34), the following imaging devices were also found to be effective for imaging MCF-FEP and measuring optical signals:

1) A flatbed scanner operating in reflectance (as opposed to transmittance) mode. Converted OPD substrate absorbance was measured in reflectance and transmittance mode on a HP Scanjet G4050 flatbed scanner and similar absorbance was seen in either mode. The term "optical interrogation" as used herein encompasses any type of optical interrogation, whether carried out in transmittance or reflectance mode.

2) A compact portable flatbed scanner. A compact, portable, USB powered, Light Emitting Diode (LED) illuminated, contact image sensor (CIS) detector, flatbed scanner (Canon LiDE model 700F) operating in transmittance mode was equally sensitive to the HP Scanjet G4050 at measuring OPD substrate.

3) A compact digital camera. A 12 megapixel Konica Minolta digital compact camera was used to take photographs of water compared with an orange aqueous solution of iodine. While the MCF-FEP filled with water showed no change in pixel intensity across the film, the orange iodine solution showed high absorbance in the blue channel. Without customising a digital compact camera to optimise detection, as little as 2 ng/ml of anti-hepatitis B core antigen was detectable simply by photographing the MCF-FEP after substrate incubation, using a standard direct ELISA protocol; sensitivity using a non-optimised digital compact camera was only 5-fold lower than when using a flatbed scanner in transmittance mode.

4) A single colour LED was found to be an effective light source for measuring absorbance of coloured substances in aqueous solutions. A stronger optical signal was seen using a compact digital camera to image MCF-FEP filled with orange coloured solutions vs water when the MCF-FEP was illuminated by a light source comprising a blue LED emitting a narrow band of wavelengths of blue light.

5) A camera integral to a smartphone (handheld mobile telephone with integral camera and computer). Anti-hepatitis B core antigen antibodies could be detected and quantified simply by photographing MCF-FEP test strips with a smartphone integrated digital camera after substrate incubation using a standard direct ELISA protocol.

6) A portable device comprising an LED plus a photo detector array.

Figure 28:
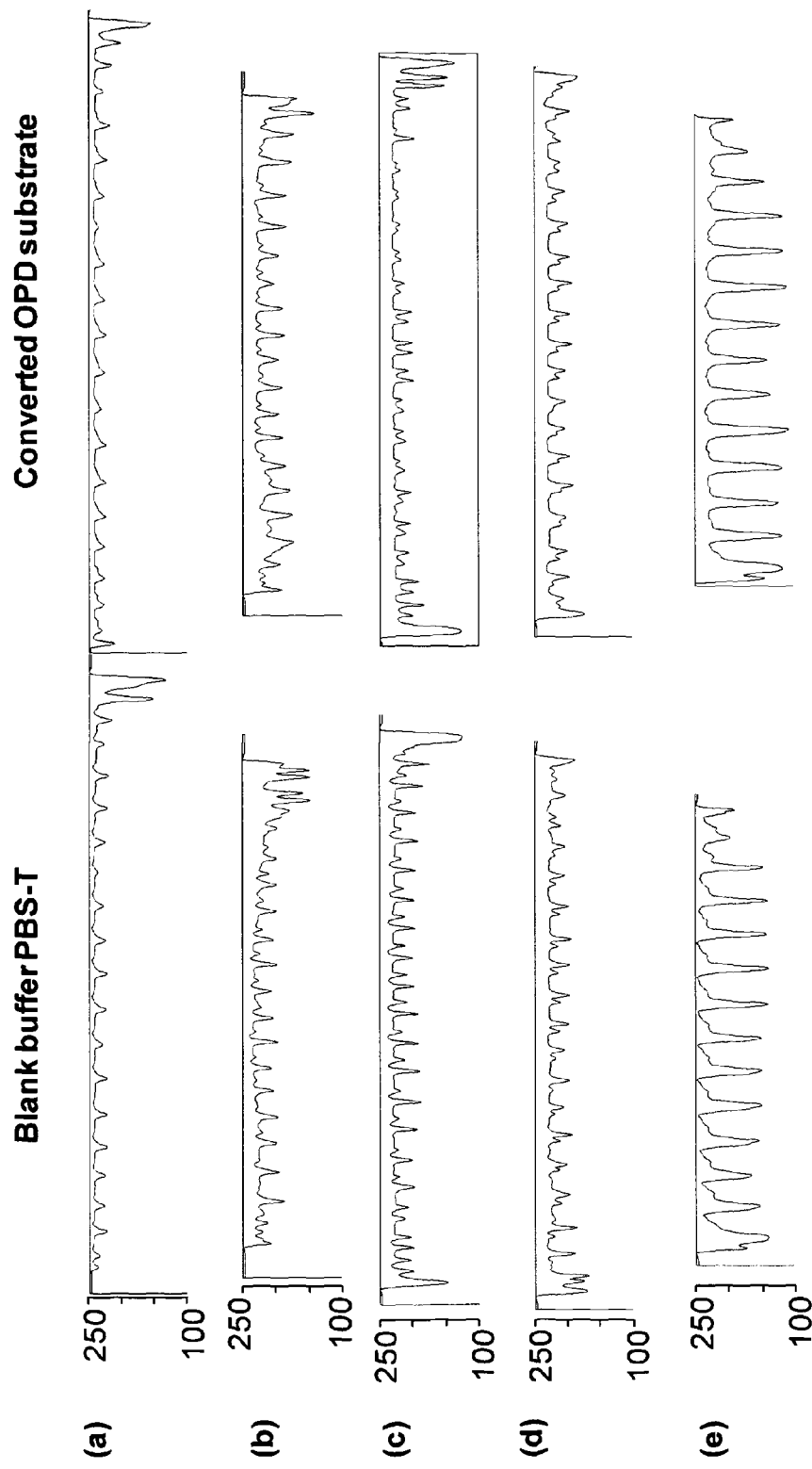
FIG. 28 shows signal detection in MCFs extruded using other thermoplastic materials in a flatbed scanner.

FIG. 28 shows signal detection in MCFs extruded using other thermoplastic materials. The optical properties of MCFs extruded from alternative thermoplastic materials were tested using the same procedure as outlined above. As shown in FIG. 28, there are optical distortions shown in the images, and these strongly affect the signal obtained by image processing. This is considered to be due to the relatively large difference in refractive index of these alternative materials compared with water. Thus, these optical distortions limit the use of these materials for quantification of the generated colour signal. The tested materials were (FIGS. 28(a)-(e): (a) MCF-EVA, (b) MCF-EVOH, (c) MCF-LV-LLDPE, (d) (c) MCF-COC, (e) MCF-HV-LLDPE. Table 1 shows the geometry of tested MCFs.

TABLE 1

Tested MCFs extruded from different thermoplastic materials

| MCF reference | Embodiment material | Mean internal diameter capillary (μm) | No. of capillaries | Refractive index |
|---|---|---|---|---|
| MCF-FEP | Fluorinated ethylene propylene (FEP) | 206 | 10 | 1.34 |
| MCF-EVA | Ethylene vinyl acetate (EVA) | 142 | 19 | 1.48 |
| MCF-EVOH | Ethylene vinyl alcohol (EVOH) | 109 | 19 | 1.51-1.52 |
| MCF-LV-LLDPE | Linear low-density polyethylene (LLDPE) | 167 | 19 | 1.51 |
| MCF-COC | Cyclic olefin copolymer (COC) | 119 | 19 | 1.53 |
| MCF-HV-LLDPE | Linear low-density polyethylene (LLDPE) | 200 | 17 | 1.51 |

As shown in FIG. 28, MCFs extruded from different thermoplastic materials with a refractive index significantly different from that of the water, a high distortion and background noise were observed, therefore impeding the use of MCFs for quantitative IAs.

Figure 29:
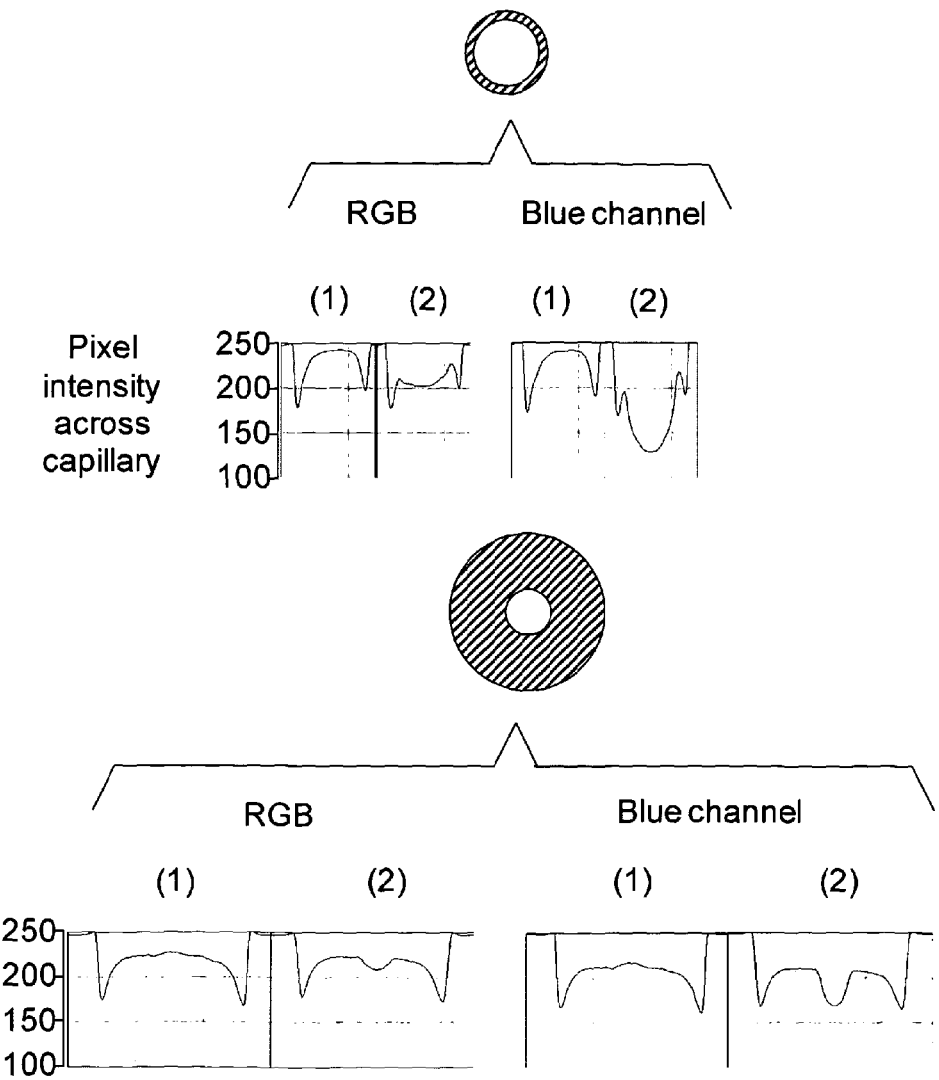
FIG. 29 shows results obtained using single-bore circular FEP capillary bodies.

FIG. 29 shows results obtained using single-bore circular FEP capillary bodies. This shows that the use of bodies having a flat geometry provides superior signal detection due to an avoidance of optical distortions. This is particular the case if it is desired to provide direct cross-interrogation of different capillaries.

The geometry of the FEP capillaries tested in FIG. 29 are shown in Table 2.

TABLE 2

Geometry of the FEP capillaries tested in FIG. 29

| Capillary | Material | O.D. (mm) | I.D. (mm) |
|---|---|---|---|
| FEP1-32x0.016 | FEP | 0.794 | 0.406 |
| FEP1-16x0.008 | FEP | 1.59 | 0.203 |

The signal detection in these circular FEP capillaries was tested using the same procedure above mentioned for FIG. 27. Capillaries of two different O.D./I.D. were tested. The high noise-to-signal ratios means the circular geometry of the capillaries is not suitable for signal detection of direct cross-interrogation of the capillary, therefore supporting the extensive use in the literature of high-power lasers for measurement of evanesced light in capillary immunoassays.

When individual circular FEP capillaries are scanned, two problems occur. For a thin capillary with a thin wall the diffraction that occurs at the sides of the capillary gives a high noise, masking the signal due to the colour of the solution in the capillary. On the other hand, for a capillary with thick walls, diffraction at the sides of the capillary body is less of a problem, however, the absorbance of the plastic gives high background masking the signal.

Thus, the preferred embodiment of the present invention (extruded microcapillary film formed from FEP) gives far superior signal-to-noise ratios than circular FEP capillaries for two reasons:

(a) Although there is diffraction and optical distortion giving high background at the edge of the film (related with the rounded edges of the MCF), the 8 capillaries in the middle are not affected at all by this edge signal.
(b) The thin plastic walls give no background absorbance allowing detection of low concentrations of absorbing dye.

FIGS. 30A, 30B, 31 and 32 demonstrate the sensitivity of the preferred embodiment of the present invention in comparison to a microtitre plate for a Hepatitis B detection assay.

All capillaries within a 2 m length of MCF-FEP were coated with Hepatitis B Core antigen, followed by blocking, washing and cutting 50 mm pieces. Each piece was attached to an individual connector and them increasing concentrations of monoclonal anti-HB-CAg sucked through all the 10 capillaries on each different piece, followed by detection with anti-mouse IgG-HRP, extensive washing, and filling with OPD substrate. After 40 minutes, the film pieces were scanned with a HP ScanJet 4050 Photo Scanner in transmittance mode.

FIG. 30A shows a schematic representation of the performed enzyme-linked immunosorbent assay in the MCF-FEP FIG. 30B shows the results obtained by scanned sections of MCF-FEP for each analysed sample. The raw RGB images were split into the red, green and blue channels. A strong light absorption was observed for the converted OPD in the blue channel. For the blue channel, a pixel intensity plot for a single line across the film is shown for comparison with the averaged plot (bottom panel). For each RGB or colour channel a plot of the averaged pixel intensity across the film as determined with ImageJ is also shown.

Figure 31:
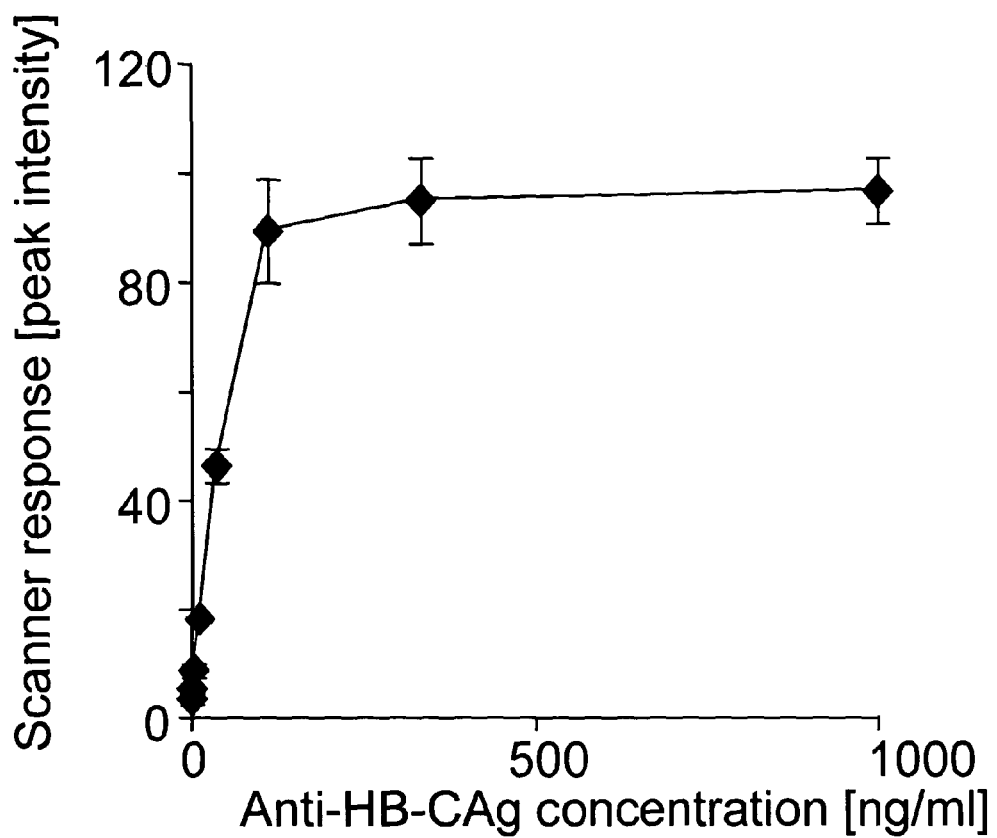
Figures 32A, 32B:
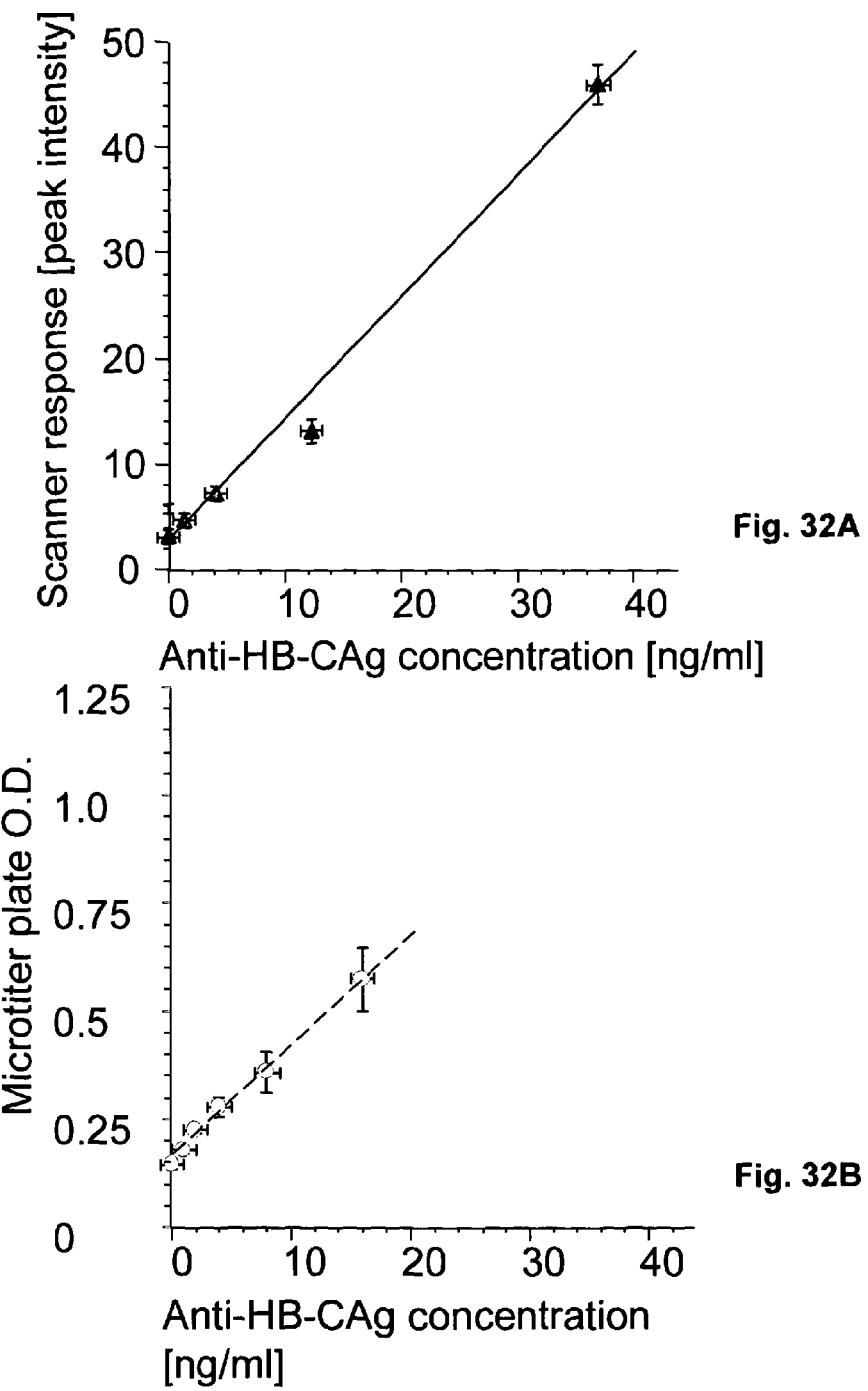
FIG. 32A shows a plot of the scanner mean peak intensity for selected samples plotted in FIG. 31 over a range of concentrations of anti-HB-CAg that show a linear relationship between scanner intensity and anti-HB-CAg concentration.
FIG. 32B shows a plot of optical density and absorbance against concentration for an ELISA was carried out in a 96-well microtitre immunoassay plate over the same range of anti-HB-CAg concentrations measured in FIG. 31 and plotted in FIG. 32A.

The individual blue absorbance peak intensities for the middle 8 capillaries seen in part FIG. 30B were measured. FIG. 31 shows a plot of mean peak intensity for all samples against concentration of anti-HB-CAg. All error bars are shown and indicate +/−1 standard deviation.

Using the same antigen, antibodies and substrate, an ELISA was carried out in a 96-well microtitre immunoassay plate. The optical density (O.D., for FIG. 32 only) or absorbance obtained for the microwell assay with a microtitre reader was plotted against concentration, and these values were compared with the scanner response over the same range of anti-HB-CAg concentrations measured in FIG. 31.

These results show that the sensitivity of an immunoassay in an MCF-FEP is identical to a conventional microtitre plate ELISA, in spite of different volumes, surface areas, processing methods, plastic material and detection method.

Figure 33:
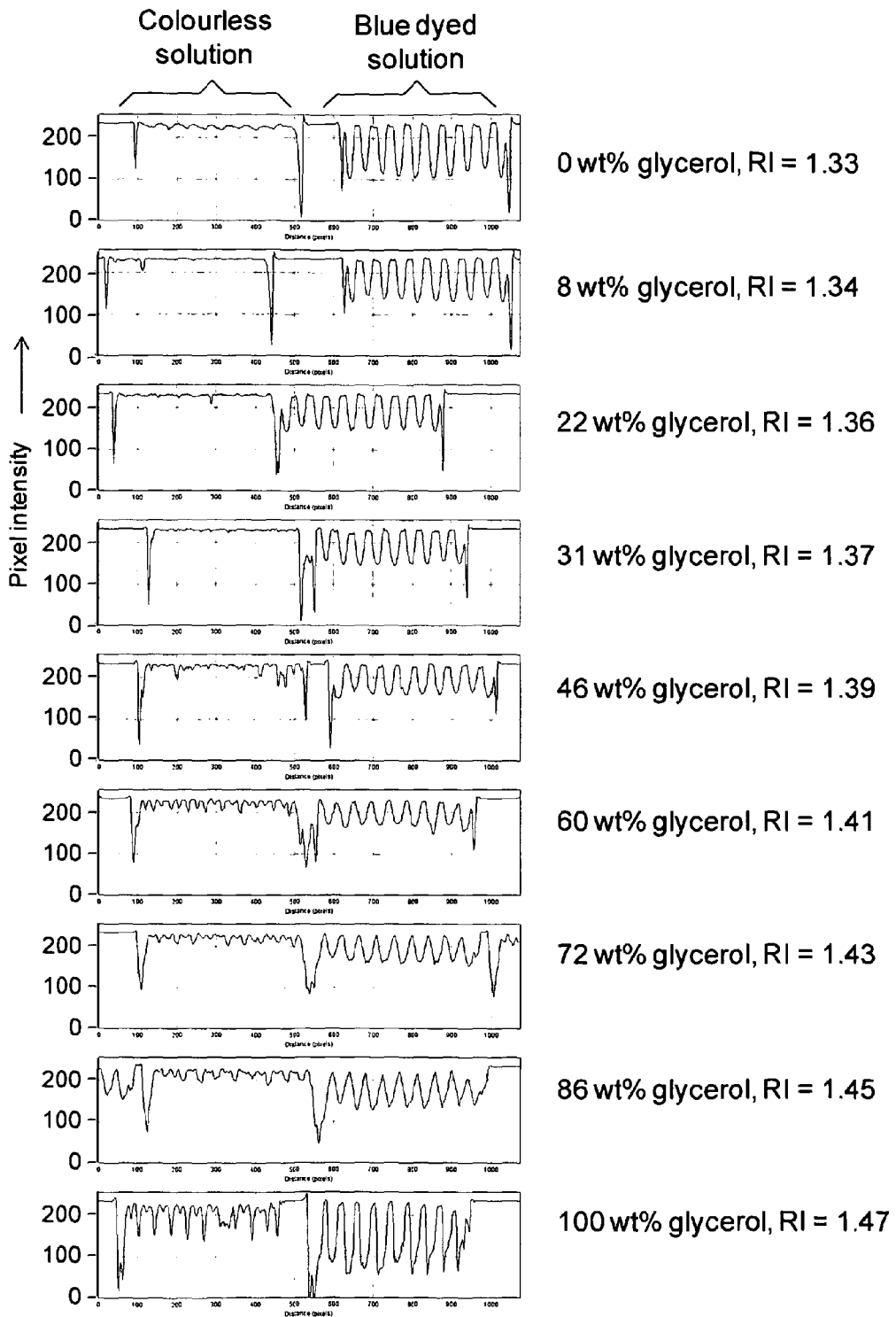
FIG. 33 illustrates the effect of the refractive index of the fluid in the profile plot for a MCF-FEP (described in Table 1).

FIG. 33 shows that scanning sections of MCF-FEP filled with different water-glycerol solutions gives different refractive index for the fluid in the range 1.33 to 1.47. The refractive index of MCF-FEP is 1.34 as summarised in Table 1. The image pairs correspond to colourless (left) and blue dyed (right) water-glycerol mixtures. Each of the blue dyed solutions included identical concentrations of blue dye. The profile plots show the variation of mean pixel intensity across the MCF-FEP sections.

Figure 34:
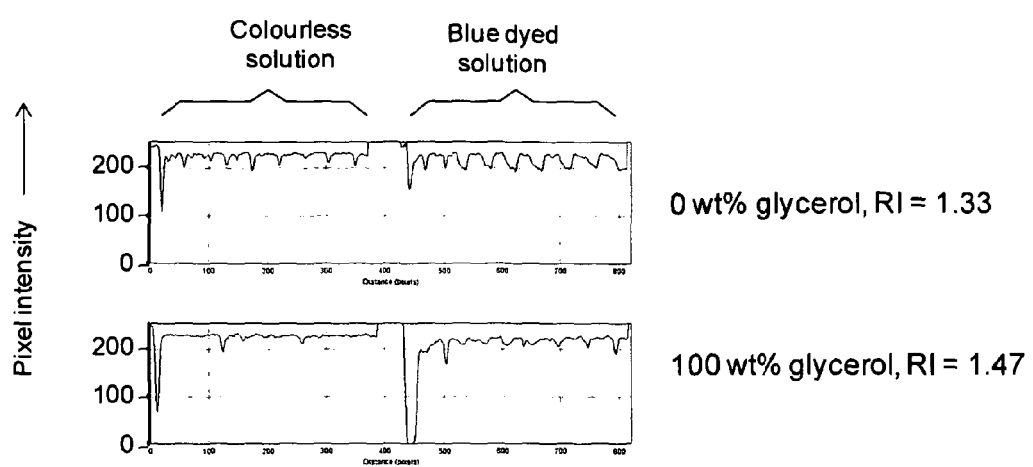
FIG. 34 illustrates the effect of the refractive index of the fluid in the profile plot for a MCF-EVA (described in Table 1).

FIG. 34 shows scanned sections of MCF-EVA filled with 0 wt % and 100 wt % of water-glycerol giving a refractive index of 1.33 and 1.47, respectively, for the fluid. The refractive index of MCF-EVA is 1.48 as summarised in Table 1. The image pairs correspond to colourless and blue dyed water-glycerol mixtures. The profile plots shows the variation of mean pixel intensity across the MCF-EVA sections. It is noted here that EVA has relatively poor light transmission properties compared with FEP. For this reason, the images in FIG. 34 do not show sharp contrast between the EVA and the blue dyed fluid.

Figure 35A:
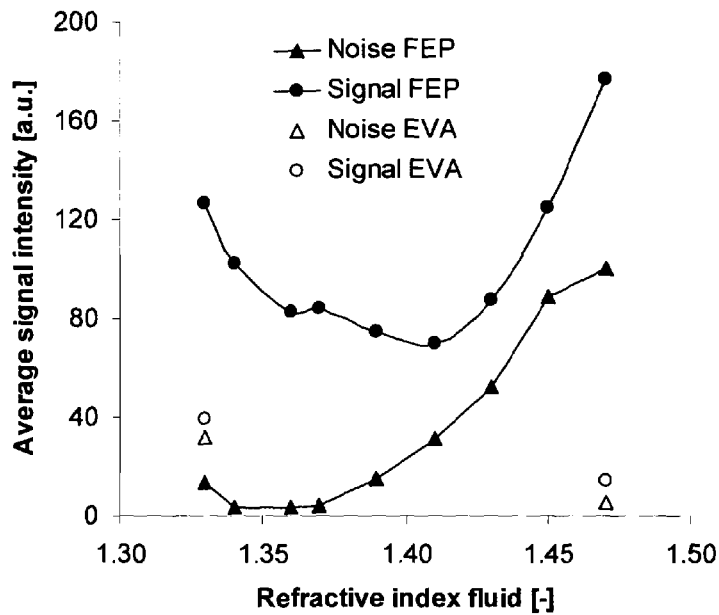
FIG. 35A summarises the variation of the signal and noise with the refractive index for MCF-FEP and MCF-EVA (as described in Table 1).

FIG. 35A summarises the variation of the mean peak height as determined from the profile plots in FIGS. 33 and 34 for the colourless (noise) and blue dyed (signal) water-glycerol mixtures in MCF-FEP and MCF-EVA at increasing refractive index of the fluid.

Figure 35B:
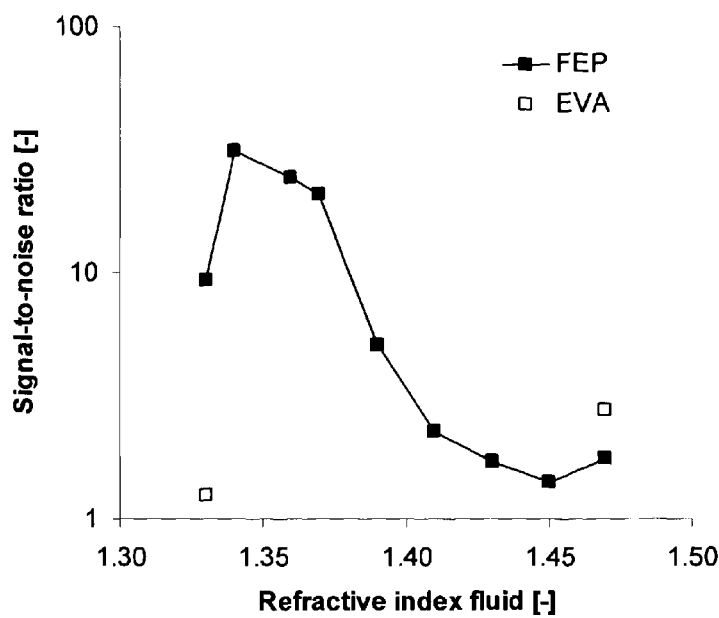
FIG. 35B summarises the variation of signal-to-noise ratio in MCF-FEP and MCF-EVA (as described in Table 1).

FIG. 35B summarises the variation of the mean signal-to-noise ratio in MCF-FEP and MCF-EVA at increasing refractive index of water-glycerol mixtures.

It is considered that the high surface-to-volume (A/V) ratios presented by individual capillaries in a MCF (up to 2 higher orders of magnitude in comparison of that in a microwell) allow the results disclosed above to be achieved for heterogeneous IAs. The large A/V ratio of capillaries allows significant savings in reagents and time to carry out an IA, because of the smaller volume and length scales for molecular diffusion in the capillaries.

EAIAs as described herein are useful for many different applications, including in health care, food processing, chemical and environmental control, and research laboratories. In particular, a major application for EAIAs is as tools for use in the diagnosis of diseases, for example in the detection of disease markers, such as cardiac or cancer biomarkers and pathogens. The simplicity of the systems disclosed herein and the requirement for only low volumes of reagents and sample fluid, makes them particularly useful for diagnostics in third-world countries and for use in research laboratories.

The preferred embodiments of the invention have been described by way of example. Modifications of these embodiments, further embodiments and modifications thereof will be apparent to the skilled person on reading this disclosure and as such are within the scope of the present invention.

REFERENCES

Zick et al., Capillary Radioimmunoassay for Insulin, Eur. J. Nucl. Med. 5, (1980) 423-425.
Healey et al., A rapid semi quantitative capillary enzyme immunoassay for digoxin, Clinica Chimica Acta, 134 (1983) 51-58.
Hemmil, Fluoroimmunoassays and Immunofluorometric Assays, Clin chem. 31/3 (1985) 359-370.
Nagainis et al., A rapid quantitative capillary tube enzyme immunoassay for human chorionic gonadotropin in urine, Clinica Chimica Acta 160 (1986) 273-219.
Shekarch et al., Capillary Enzyme Immunoassay for Rapid Detection of Herpes Simplex Virus in Clinical Specimens, Journal of clinical microbiology (1987) 320-322.
Misiakos & Kakabakos, A multi-band capillary immunosensor, Biosensors & Bioelectronics 13 (1998) 825-830.
Rose et al., GDH biosensor based off-line capillary immunoassay for alkylphenols and their ethoxylates, Biosensors and Bioelectronics 17 (2002) 1033-1043.
Mastichiadis at al., Simultaneous Determination of Pesticides Using a Four-Band Disposable Optical Capillary Immunosensor, Anal. Chem. (2002) 74 (23) 6064-6072.
Petrou et al., Multi-analyte capillary immunosensor for the determination of hormones in human serum samples, Biosensors & Bioelectronics 17 (2002) 261-268.
Bange et al., Microfluidic immunosensor systems, Biosensors and Bioelectronics 20 (2005) 2488-2503
Lionello et al., Protein adsorption in static microsystems: effect of the surface to volume ratio, Lab Chip (2005) 5, 254-260.
Herrmann et al., Enzymatically-generated fluorescent detection in micro-channels with internal magnetic mixing for the development of parallel microfluidic ELISA, Lab Chip (2006) 6, 555-560.
Yager et al., Microfluidic diagnostic technologies for global public health, Nature, 442(27) (2006)
Yacoub-George et al., Automated 10-channel capillary chip immunodetector for biological agents detection, Biosensors and Bioelectronics 22 (2007) 1368-1375.
Henares at al., Multiple enzyme linked immunosorbent assay system on a capillary-assembled microchip integrating valving and immuno-reaction functions, Analytica Chimica Acta 589 (2007) 173-179.
Mastichiadis at al., Capillary-based immunoassays, immunosensors and DNA sensors—steps towards integration and multi-analysis, Trends in Analytical Chemistry, Vol. 27, No. 9, (2008).
Schroeder et al., User Configurable Microfluidic Device for Multiplexed Immunoassays Based on DNA-Directed Assembly, Anal. Chem. (2009) 81 (3) 1275-1279.

The invention claimed is:

1. A device for carrying out an immunoassay, the device having:
a unitary body with an exterior surface, and at least two microcapillary bores extending internally along the unitary body, wherein for each microcapillary bore a population of first members of a respective specific binding pair is immobilised at least at a portion of a inner surface of the microcapillary bore, each first member being capable of specifically binding with a second member of the respective specific binding pair, wherein the unitary body is substantially transparent to visible light to allow optical interrogation of the microcapillary bores, and wherein the device is formed from a fluorinated polymer having a refractive index which is in the range of 1.26 to 1.40, the refractive index being measured at 20° C. with light of wavelength 589 nm, and wherein the device is an extruded microcapillary film.

2. The device according to claim 1 wherein each of the at least two microcapillary bores has an inner diameter of at least 10 μm and less than 1 mm.

3. The device according to claim 1 wherein one microcapillary bore in the device has a differently-treated inner surface from at least one other microcapillary bore in the device, the difference in surface treatment providing a measurable difference in immunoassay performance between the microcapillary bores.

4. The device according to claim 3 wherein said differently treated inner surface comprises a different concentration of first members adsorbed at its surface compared with said at least one other microcapillary bore.

5. The device according to claim 3 wherein said differently treated inner surface comprises a first members of a different specific binding pair adsorbed at its surface compared with said at least one other microcapillary bore.

6. The device according to claim 1 wherein two or more of the at least two microcapillary bores have identically-treated inner surfaces, in order to provide measurement redundancy in the device.

7. The device according to claim 1 wherein two or more of the at least two microcapillary bores have identically-treated inner surfaces and one or more other microcapillary bores in the same device has a differently-treated inner surface.

8. The device according to claim 1 wherein the exterior surface of the body includes a measurement first surface and a measurement second surface, so that in use, light is transmitted through the device from the measurement first surface to the measurement second surface, at least one of the measurement first surface and the measurement second surface extending substantially parallel with the principal axes of the two or more microcapillary bores.

9. The device according to claim 8 wherein the measurement first surface and the measurement second surface are substantially planar.

10. The device according to claim 1 wherein the exterior surface of the body includes a measurement first surface and a measurement second surface, so that in use, light is transmitted through the device from the measurement first surface to the measurement second surface, both of the measurement first surface and the measurement second surface extending substantially parallel with the principal axes of the two or more microcapillary bores.

11. The device according to claim 1, wherein the population of the first members is substantially uniformly immobilised along a length of each microcapillary bore.

12. The device according to claim 1, wherein each microcapillary bore has an internal diameter of 50 μm to 400 μm and a length of 5 mm to 50 mm.

13. The device according to claim 1, wherein each microcapillary bore has a circular cross-sectional shape.

14. The device according to claim 1, wherein each microcapillary bore has an oval cross-sectional shape.

15. The device according to claim 1, wherein all or the portion of the inner surface of the at least two microcapillary bores is hydrophobic.

16. The device according to claim 1, wherein the first members are selected from the group consisting of proteins, polysaccharides, nucleic acid molecules, and small molecules.

17. The device according to claim 1, wherein the first members are selected from the group consisting of antigens, antibodies or antibody fragments thereof, biotin, avidin, receptors, ligands, enzymes, and enzyme substrates.

18. The device according to claim 17, wherein the ligands are hormones and the receptors are hormone receptors.

19. The device according to claim 17, wherein the antibody fragments are selected from the group consisting of Fab, Fd, Fv, dAb, isolated CDR regions, F(ab')2, Fab', Fab'-SH, scFv, a bispecific single chain Fv dimers; and diabodies.

20. The device according to claim 1, wherein the device has a thickness in the range of 0.2 mm to 2 mm.

21. The device according to claim 1, wherein the fluorinated polymer is selected from the group consisting of fluorinated ethylene polypropylene (FEP), tetrafluoroethylene hexafluoropropylene vinylidene fluoride (THV), perfluoroalkoxy (PFA), ethylene tetrafluoroethylene (ETFE), and poly(chlorotrifluoroethylene) (PCTFE).

22. The device according to claim 1, wherein the inner diameter of the bore varies less than 10% along the length of the device.

* * * * *